United States Patent
Shadmehr et al.

(10) Patent No.: US 10,518,092 B2
(45) Date of Patent: Dec. 31, 2019

(54) SYSTEM AND METHOD FOR BRAIN STIMULATION FOR IMPROVEMENT OF MOTOR SYMPTOMS IN PARKINSON'S DISEASE AND OTHER MOVEMENT DISORDERS

(71) Applicant: THE JOHNS HOPKINS UNIVERSITY, Baltimore, MD (US)

(72) Inventors: Reza Shadmehr, Ellicott City, MD (US); Yousef Salimpour, Baltimore, MD (US); Zoltan Mari, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 63 days.

(21) Appl. No.: 15/506,538

(22) PCT Filed: Aug. 26, 2015

(86) PCT No.: PCT/US2015/046900
§ 371 (c)(1),
(2) Date: Feb. 24, 2017

(87) PCT Pub. No.: WO2016/033159
PCT Pub. Date: Mar. 3, 2016

(65) Prior Publication Data
US 2017/0291030 A1   Oct. 12, 2017

Related U.S. Application Data

(60) Provisional application No. 62/041,694, filed on Aug. 26, 2014, provisional application No. 62/050,891, (Continued)

(51) Int. Cl.
*A61N 1/36* (2006.01)
*A61N 1/20* (2006.01)

(52) U.S. Cl.
CPC .......... *A61N 1/36132* (2013.01); *A61N 1/20* (2013.01); *A61N 1/36025* (2013.01);
(Continued)

(58) Field of Classification Search
CPC .. A61N 1/36014; A61N 1/20; A61N 1/36025; A61N 1/36028; A61N 1/3603;
(Continued)

(56) References Cited

U.S. PATENT DOCUMENTS 8,583,238 B1    11/2013   Heldman
8,706,241 B2    4/2014    Firlik et al.
(Continued)

OTHER PUBLICATIONS

Benninger DH, et al., (2010) Transcranial direct current stimulation for the treatment of Parkinson's disease. J Neurol Neurosurg Psychiatry 81:1105-1111.
(Continued)

*Primary Examiner* — George R Evanisko
(74) *Attorney, Agent, or Firm* — Johns Hopkins Technology Ventures

(57) ABSTRACT

An embodiment in accordance with the present invention is directed to a system and device for applying electrical direct current transcranially to the brain that is combined with a behavioral activity consisting of an isometric force production task. The device is non-invasive or implantable and serves to improve motor symptoms in Parkinson's disease (PD) and other movement disorders. During the stimulation, the patient is engaged in a behavioral task using a system consisting of two force transducers and a controller. The patient holds the transducers, one in each hand, and is engaged in a task that requires the brain to assign forces to each arm so that the sum of the forces matches an instructed amount. In an electrode placement specifically for PD, bilateral primary motor cortices are simultaneously stimulated according to a specific algorithm that depends on the (Continued)

forces that the PD affected individual produces in the behavioral task.

7 Claims, 25 Drawing Sheets

Related U.S. Application Data filed on Sep. 16, 2014, provisional application No. 62/118,735, filed on Feb. 20, 2015.

(52) U.S. Cl.
CPC ..... *A61N 1/36067* (2013.01); *A61N 1/36103* (2013.01); *A61N 1/36125* (2013.01)

(58) Field of Classification Search
CPC ............ A61N 1/36031; A61N 1/36021; A61N 1/36082; A61N 1/36103; A61N 1/36067; A61B 5/1125

See application file for complete search history.

(56) References Cited

U.S. PATENT DOCUMENTS

| | | |
|---|---|---|
| 2010/0087698 A1 | 4/2010 | Hoffman |
| 2013/0096363 A1 | 4/2013 | Schneider et al. |
| 2014/0058189 A1 | 2/2014 | Stubbeman |
| 2014/0200432 A1* | 7/2014 | Banerji ................ A61B 5/0488 600/383 |

OTHER PUBLICATIONS

Fregni F, et al.,(2006) Noninvasive cortical stimulation with transcranial direct current stimulation in Parkinson's disease. Mov Disord 21:1693-1702.

Fritsch B, et al., (2010) Direct current stimulation promotes BDNF-dependent synaptic plasticity: potential implications for motor learning. Neuron 66:198-204.

Kuo MF, et al., (2008) Boosting focally-induced brain plasticity by dopamine. Cereb Cortex 18:648-651.

Salimpour Y, et al., (2014) Motor costs and the coordination of the two arms. J Neurosci 34:1806-1818.

Valentino et al., (2014) Transcranial Direct Current Stimulation for Treatment of Freezing of Gait: A cross-over Study. Movement Disorders, vol. 29, No. 8.

Verheyden et al., (2013) Immediate Effect of Transcranial Direct Current Stimulation on Postural Stability and Functional Mobility in Parkinson's Disease. Movement Disorders, vol. 28, No. 14.

Wu et al., (2008) Noninvasive Brain Stimulation for Parkinson's Disease and Dystonia. Neurotherapeutics: The Journal of the American Society for Experimental NeuroTherapeutics. vol. 5, 345 361.

* cited by examiner

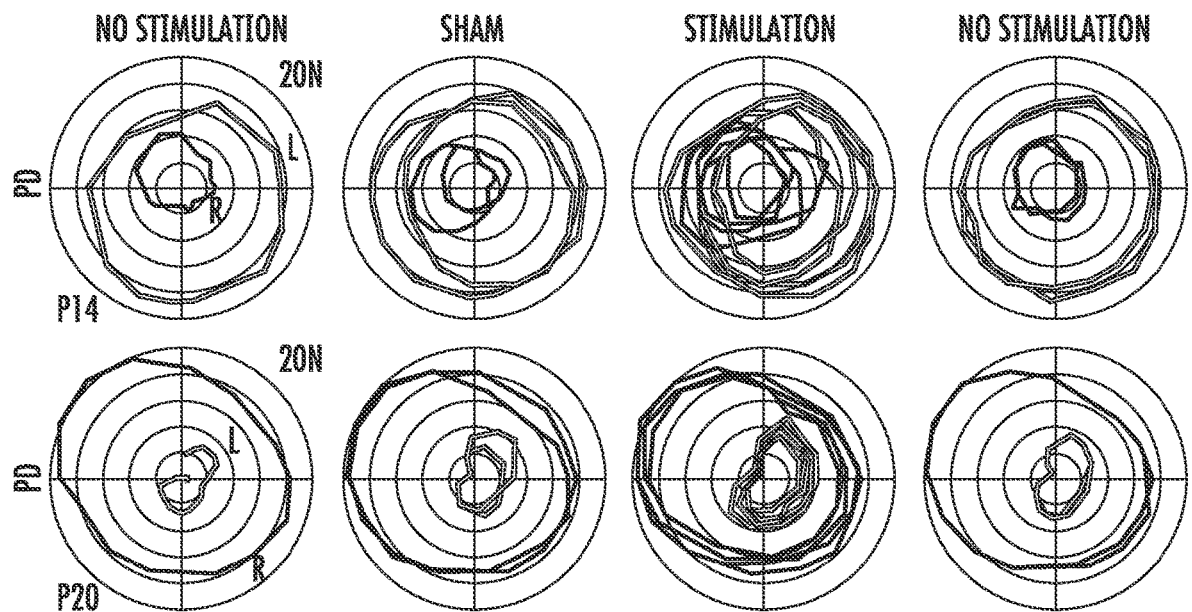
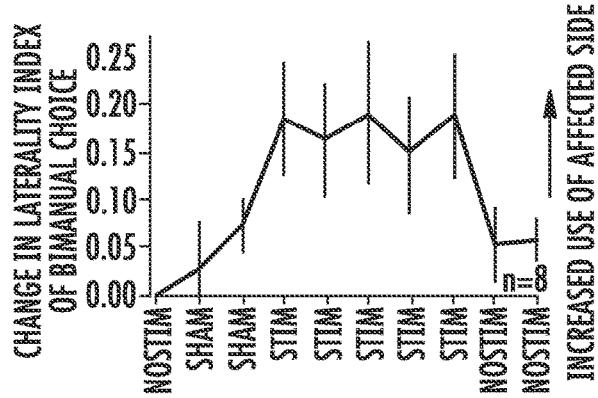
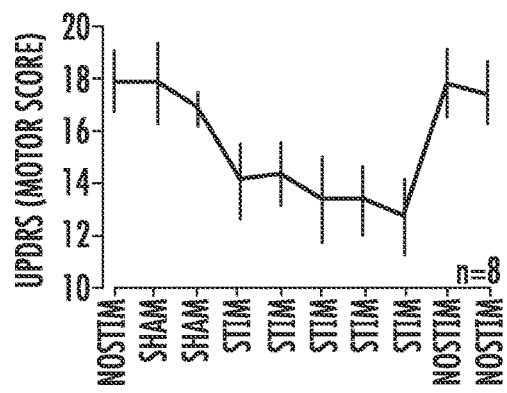
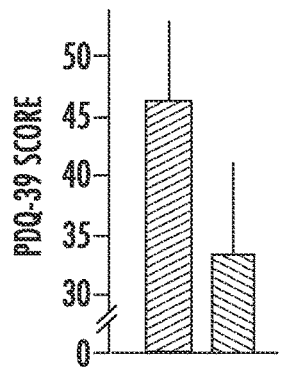
FIG. 9A
FIG. 9B
FIG. 9C
FIG. 9D

US 10,518,092 B2

SYSTEM AND METHOD FOR BRAIN STIMULATION FOR IMPROVEMENT OF MOTOR SYMPTOMS IN PARKINSON'S DISEASE AND OTHER MOVEMENT DISORDERS

CROSS-REFERENCE TO RELATED APPLICATIONS

This application is a 35 U.S.C. § 371 U.S. national entry of International Application PCT/US2015/046900, having an international filing date of Aug. 26, 2015, which claims the benefit of U.S. Provisional Application No. 62/041,694, filed Aug. 26, 2014, U.S. Provisional Patent Application No. 62/050,891, filed Sep. 16, 2014, and U.S. Provisional Patent Application No. 62/118,735, filed Feb. 20, 2015, the content of each of the aforementioned applications is herein incorporated by reference in their entirety.

FIELD OF THE INVENTION

The present invention relates generally to treatment of symptoms for Parkinson's disease (PD). More particularly, the present invention relates to a system and method for transcranial brain stimulation in which the pattern of stimulation relies on motor measurements from isometric force production of the two arms of the PD patient.

BACKGROUND OF THE INVENTION

PD is a movement disorder characterized by progressive degeneration of various neural structures, including parts of the basal ganglia and the cerebral cortex. In the United State, at least 500,000 people suffer from PD, with 50,000 new patients diagnosed each year. Worldwide, PD directly affects 4.1 million people. There are currently no treatments that cure, reverse, prevent, or slow the progression of PD.

Available treatments for PD currently include medication and deep brain stimulation (DBS), both of which mask the symptoms without changing the underlying pathology or pathophysiology. These treatment modalities each have significant limitations. Medication, which involves dopamine therapy (e.g., L-dopa), may be poorly tolerated due to its side effects, and its use can be limited by the short duration of action at later stages of disease. Furthermore, prolonged L-dopa use leads to disabling motor complications. Pharmacotherapy options besides L-dopa offer less potent symptom control and are often associated with undesirable side effects. At this stage, many patients undergo a DBS procedure which can help the motor complications as well as provide symptomatic relief beyond pharmacotherapy. However, in addition to risks inherent to invasive brain surgery, there are potential side effects, including speech impairment, worsening gait and balance, as well as cognitive and behavioral complications of DBS. As a result of limitations with these treatments, a novel approach to management of PD is needed: one that can extend the time period from medication to DBS horizon, or reduce the rate of increase in the reliance on medication.

An approach that has been attempted but produced puzzling results is transcranial direct current stimulation (tDCS). tDCS is a non-invasive procedure in which direct current (typically 1-2 mA) is passed through anode and cathode electrodes that are placed on the head and localized using MRI, transcranial magnetic stimulation (TMS), or EEG. A study examined patients in the moderate stage who were off medication for 12 hours and found that application of anodal tDCS over the left primary motor cortex (M1) produced 20% improvement of clinical motor scores (as compared to sham stimulation). This form of tDCS was found to reduce motor symptoms, but only in patients who were off their medication. Unfortunately, patients suffer when they are off their medication, so this result is interesting but only of limited clinical relevance.

A later double-blind study also applied anodal stimulation to the left M1 and measured the time it took for the patients to perform 10 elbow flexion movements and walk a fixed. In this study, the authors found that stimulation decreased walk time (the primary outcome) compared to sham, but only when tested off medication and after exclusion of an outlier. Furthermore, motor symptoms and time to perform the elbow task did not differ between sham and real stimulation.

However, it may be possible, if the technique is applied properly, that tDCS would lead to motor improvement in the medication ON state as well, which is more clinically relevant: (1) real life patients outside of experimental settings will be on medications; (2) if their maximum symptomatic benefits on optimized pharmacotherapy are still not satisfactory, only a treatment beyond what drugs can do will help.

Parkinson's disease is a progressive disease. Any symptom control treatment should be used for a long term and it should be independent to the disease stage. The treatment should not interfere with normal daily life of the patient and be applicable in any time even during the sleep time. It also should be very easy to use with minimum effort requirement from patient regarding electrode placement and stimulation parameter settings.

Accordingly, it would therefore be beneficial to improve motor symptoms in PD without having to take patients off of medication. It would also be beneficial to provide a device and system for long term use in the improvement of motor symptoms in PD and other movement disorders with brain stimulation therapy without the patient having to be involved in the device preparatory process and electrode placement. tDCS is a low cost, low risk procedure that if found effective, can be scaled to a large market, particularly in developing countries where costs and technology loom as barriers to adoption.

SUMMARY OF THE INVENTION

The foregoing needs are met, to a great extent, by the present invention which provides a system for treatment of Parkinson's disease including a controller, a force transducer component, and a transcranial direct current stimulation component. The force transducer component is configured to accept force from the left hand of the subject and the right hand of the subject simultaneously. The force transducer component is configured to transmit data related to the measured force to the controller, and the force transducer component is configured to receive instructions from the controller regarding a predetermined force value that the subject is asked to create. The transcranial direct current stimulation component is configured to apply transcranial direct stimulation to motor cortices of the subject. The transcranial direct current stimulation component includes an anode and a cathode electrode. The conducting component of each electrode is a small sponge that is soaked in saline. One of the electrodes is placed over the left motor cortex of the person affected by Parkinson's disease, while the other electrode is placed over the right motor cortex. The critical and novel idea is to use the force transducers to measure patterns of force produced by the patient, and then from that measurement determine the pattern of stimulation on each motor cortex. The transcranial direct current stimulation component is configured to receive input from the controller regarding the stimulation to be applied and transmits data to the controller related to the stimulation applied.

In accordance with an aspect of the present invention, the system includes a display screen for the force transducer component such that the subject can visualize the force to be applied to the transducers. The system also includes a headband for positioning the anode and the cathode and holding the transcranial direct current stimulation component on a head of the subject. Communication between the transcranial direct current stimulation component and the controller is wireless. The controller can take the form of a computing device, and the computing device can include a non-transitory computer readable medium. The non-transitory computer readable medium is programmed to integrate the force transduction component and the transcranial direct stimulation component.

In accordance with another aspect of the present invention, a method for treatment of Parkinson's disease in a subject includes soliciting the subject to apply force to a force transduction component so that the sum of the forces produced by the two hands equals a target amount. The brain of the patient determines how much force to produce with each hand so that the sum equals the solicited amount. The system solicits a force vector at a number of directions, measuring the force produced by the left and right arms for each of the solicited directions. From the pattern of recorded forces, a laterality index L is determined:

$$L = \frac{1}{n}\sum_{i=1}^{n} \frac{f_R^{(i)} - f_L^{(i)}}{f_R^{(i)} + f_L^{(i)}} \quad (1)$$

In Eq. (1), $f_R^{(i)}$ is the force measured from the right hand on trial i, and $f_L^{(i)}$ is the force measured from the left hand.

If the laterality index is less than one, the controller will apply +2 mA current to the right primary motor cortex for 30 minutes while the patient is directed to continue production of force in various directions. That is, when the laterality index is less than one, the electrode positioned on the right motor cortex will act as the anode, and the electrode positioned on the left motor cortex will act as the cathode.

If the laterality index is greater than one, the controller will apply +2 mA current to the left primary motor cortex for 30 minutes while the patient is directed to continue production of force in various directions. That is, when the laterality index is greater than one, the electrode positioned on the left motor cortex will act as the anode, and the electrode positioned on the right motor cortex will act as the cathode.

In accordance with yet another aspect of the present invention, the method is executed by a non-transitory computer readable medium. The method also includes displaying a force to be applied to the force transduction component to the subject.

In accordance with still another aspect of the present invention, a system for applying electrical current to the brain transcranially includes a transdermally implantable component. The transdermally implantable component includes a stimulator having a cathode and an anode. The cathode and anode are configured to provide a unifocal stimulation to a target area of the brain. The transdermally implantable component includes a power transceiver module configured for receiving power and for receiving and transmitting data, and the transdermally implantable component includes a dose controller for managing the stimulation provided to the target area of the brain. The system also includes a main external component having a power and data transducer for providing power and data to the power transceiver module of the transdermally implantable component. The main external component also includes a dose monitor and input module for changing and transmitting dosages for stimulation of the target area of the brain.

In accordance with yet another aspect of the present invention, a battery is used for providing power to the power and data transducer. The battery is rechargeable and the system includes a recharging module. The system can include four cathodes and one anode. A ring shaped configuration can be employed placing the cathodes around the anode. The system includes a user interface and a computer. The computer is configured to communicate with the external main component. The computer is also configured to communicate with the external main component regarding dosing for the stimulation. A radius of the ring shaped configuration around the anode is related to focality of treatment.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 9A-9D illustrate graphical views of results of a 10-day study, in which 8 PD affected individuals participated and received sham or real stimulation, resulting in changes in force measurements, clinical scores, and subjective measure of quality of life (PDQ-39 score), according to an embodiment of the present invention.

DETAILED DESCRIPTION

Figure 1:
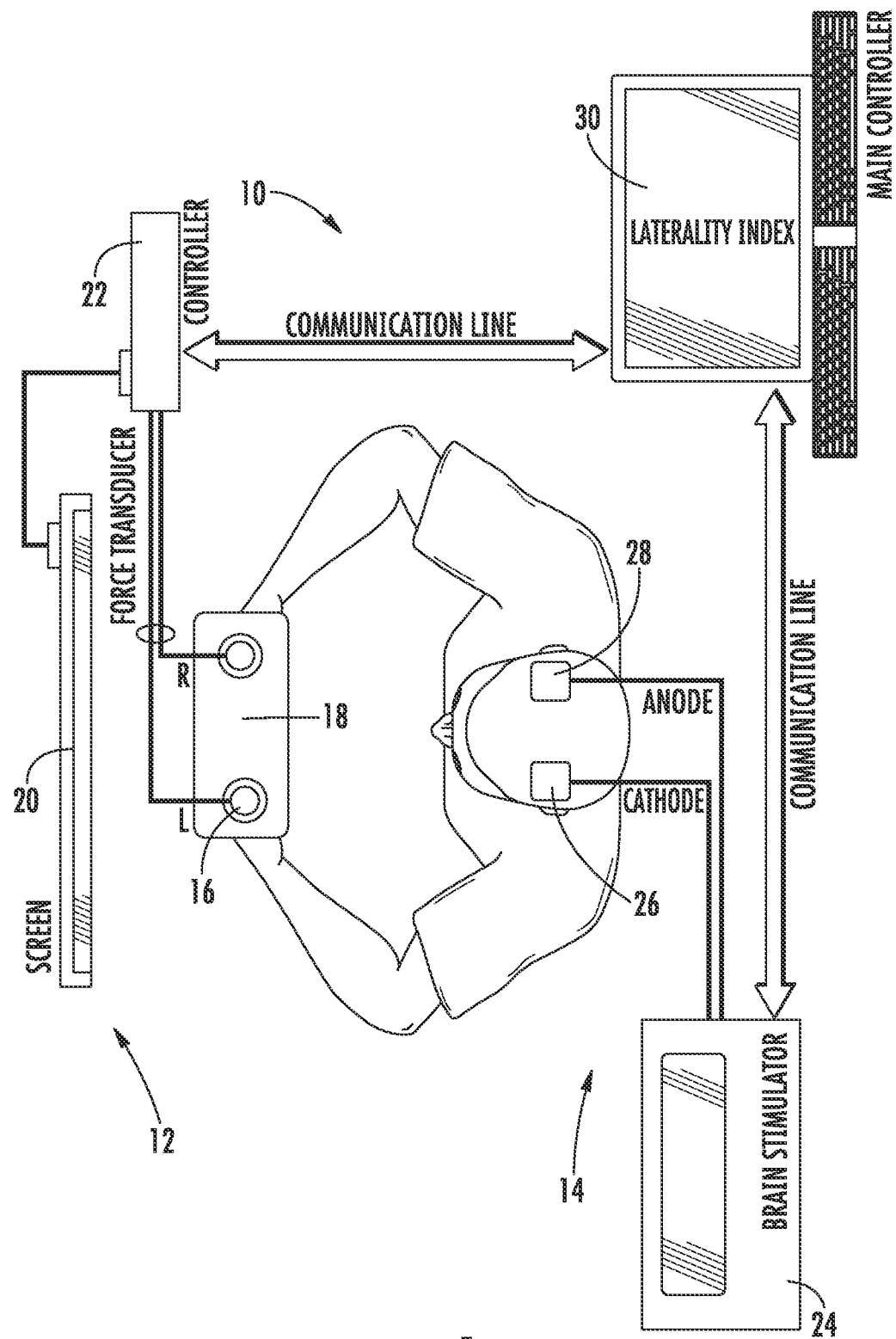
FIG. 1 illustrates a schematic diagram of system for delivery of transcranial direct current stimulation and integration of transcranial direct current stimulation and the behavior task, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention is directed to a system and device for applying electric current transcranially to the brain that is combined with a behavioral activity consisting of an isometric force production task. The system and device is designed to improve motor symptom in Parkinson's disease (PD). In a unique electrode placement and stimulation technique specifically for PD, both motor cortices are simultaneously stimulated by in a pattern that depends on the force measurements taken by the force transducers in a behavioral task. During the stimulation, the patient is engaged in the behavioral task using a system consisting of two force transducers and a controller. The patient holds the transducers, one in each hand, and is engaged in a task that requires the brain to assign forces to each arm in such a way so that the sum of the forces matched an instructed amount. From the force measurements, a laterality index is computed (Eq. 1). This laterality index determines the pattern of stimulation that is applied to each electrode.

The present invention is based on the failings of previous tDCS stimulation techniques, which were ineffective in reducing motor symptoms of medicated PD patients. This yielded the new montage of tDCS stimulation of the present invention. In the technique of the present invention, both motor cortices are simultaneously stimulated. The specific locations of the brain that are stimulated and the pattern of stimulation are important aspects of the present invention. One electrode is placed over the right motor cortex and the other over the left motor cortex. The pattern of stimulation varies based on the disease state of the patient, as assayed by the forces that they produce in the behavioral task. If the laterality index is negative, +2 mA anodal stimulation is used over the right motor cortex, with the left motor cortex acting as the cathode electrode. If the laterality index is positive, +2 mA anodal stimulation is used over the left motor cortex, with the right motor cortex acting as the cathode electrode. This specific form of stimulation is effective in improving symptoms in both right- and left-side affected PD, but other forms of stimulation can be ineffective, and in some cases lead to worsening of symptoms. Roughly speaking, a right-side affected PD individual will generally (but not always) exhibit a negative laterality index, and a left-side affected PD individual will generally (but not always) exhibit a positive laterality index. The critical aspect of the present invention is that the actual force patterns produced by the patient will be used to determine the pattern of cortical stimulation. A second novel component of the present invention is the coupling of our stimulation with a behavioral task that attempts to engage cortical plasticity during the stimulation, resulting in a hypothetical increase in the neuronal pool size available in the motor cortex for control of the contralateral limb.

FIG. 1 illustrates a schematic diagram of a system for delivery of transcranial direct current stimulation and integration of transcranial direct current stimulation and the behavior task, according to an embodiment of the present invention. As illustrated in FIG. 1, the system 10 includes a force transduction component 12 and a stimulation component 14. The force transduction component 12 includes two force transducers 16, 18 with a display 20 to provide a framework for subject to do isometric force production task in a specific manner. The two force transducers 16, 18 are configured such that one force transducer 16 is held in the left hand of the subject and the other force transducer 18 is held in the right hand of the subject. A force controller 22 is coupled to the two force transducers 16, 18 and the display. The force controller 22 receives force information from the force transducers 16, 18 and transmits data to the display 20 and other controllers.

FIG. 1 also illustrates a transcranial direct current stimulation component 14 integrated into the system for the purpose of having brain stimulation according to the laterality index. The transcranial direct current stimulation component 14 includes a brain stimulator 24, a cathode 26, an anode 28, and a main controller 30. The brain stimulator 24 provides electrical current to the cathode 26 and the anode 28, as specified by the main controller 30. The brain stimulator 24 and the main controller 30 are configured to be in communication with one another, such that the brain stimulator 24 receives input on stimulation levels and the main controller 30 receives output from the brain stimulator 24 regarding those stimulation levels. The main controller 30 is also in communication with the force controller 22. This allows for integration of the force transduction task with the transcranial direct current stimulation.

As illustrated in FIG. 1, the patient has a negative laterality index. Therefore, the brain stimulator delivers +2 mA to the electrode placed on the right motor cortex, and sets the electrode on the left motor cortex to act as the ground. That is, the right motor cortex electrode is the anode, whereas the left motor cortex electrode is the cathode. The reason for this particular pattern of stimulation is that the laterality index, as determined by the force production in the behavioral task, is negative. If the patient has a positive laterality index, the brain stimulator would deliver +2 mA to the electrode placed on the left motor cortex, and set the electrode on the right motor cortex to act as the ground. That is, in this case the left motor cortex electrode is the anode, whereas the right motor cortex electrode is the cathode.

Figure 2:
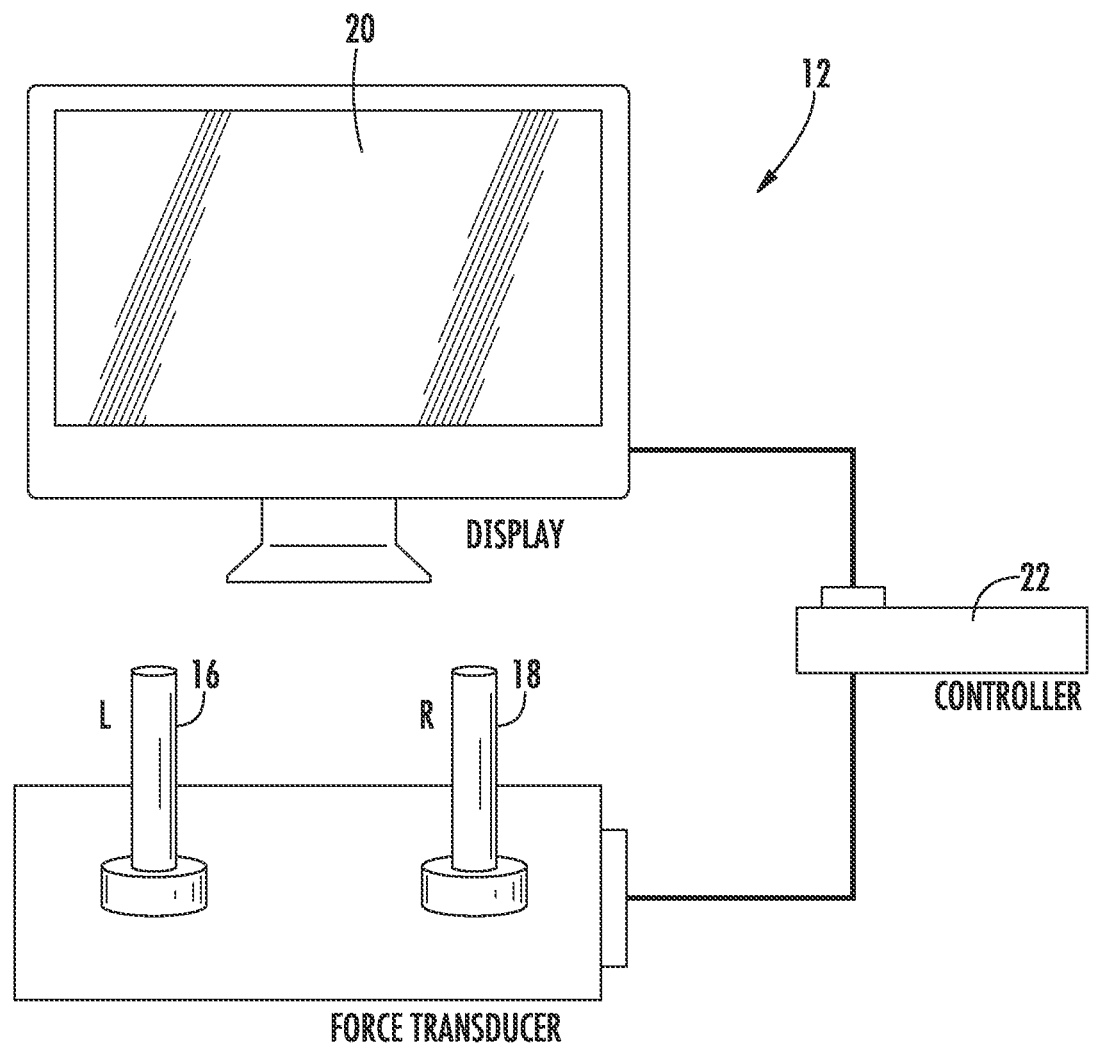
FIG. 2 illustrates a schematic diagram of the force transduction component of the system, for isometric force production, according to an embodiment of the present invention.

FIG. 2 illustrates a schematic diagram of the force transduction component of the system, according to an embodiment of the present invention. The force transduction component 12 includes two force transducers 16, 18, the display 20 and the force controller 22. FIG. 2 illustrates the components from the perspective of the patient who will be using the system. The force controller 22 is designed in such a way that the timing of brain stimulation is synchronized with the behavioral task. The isometric force production task designed and implemented in main controller and executable by subject in force transducers based on screen feedback.

Figure 3:
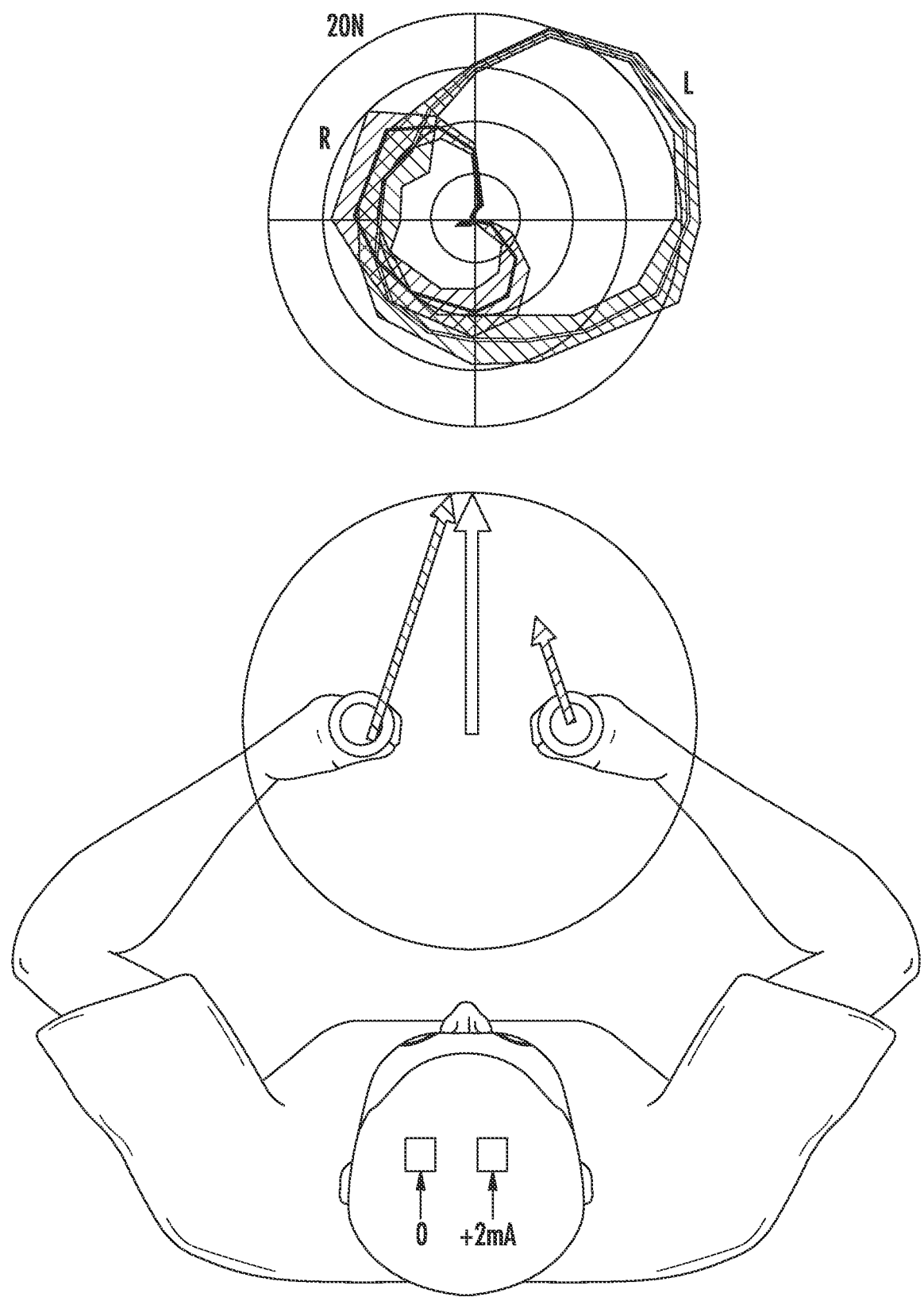
FIG. 3 illustrates a top down view of a subject engaging with the force transduction component, example of the force produced in the behavioral task, and the resulting current produced by the transcranial direct current device, according to an embodiment of the present invention.

FIG. 3 illustrates a top down view of a subject engaging with the force transduction component, according to an embodiment of the present invention. In accordance with the present invention, the subject holds the handles of two force transducer equipped handles, one in each hand. The goal is to generate force with the left and the right arms in such a way as to move a cursor toward targets distributed around a circle, producing a force that matches an instructed amount (20 Newtons of force). The position of the cursor is the sum of the force vectors produced by each arm, and so the brain is free to choose the amount of force it wishes to produce with each arm. For each direction of target the subjects chooses how much force to produce with their right and left arms. The controller senses these choices and uses the patterns to compute the laterality index. As illustrated in FIG. 3, this subject generally produces more force with the left arm than the right arm. This means that the laterality index for this subject will be negative. This determination of the laterality index is critical for the choice of the pattern of cortical stimulation with tDCS. The present invention also works to engage cortical plasticity to increase the neuronal pool size available for control of the contralateral limb.

Figure 4:
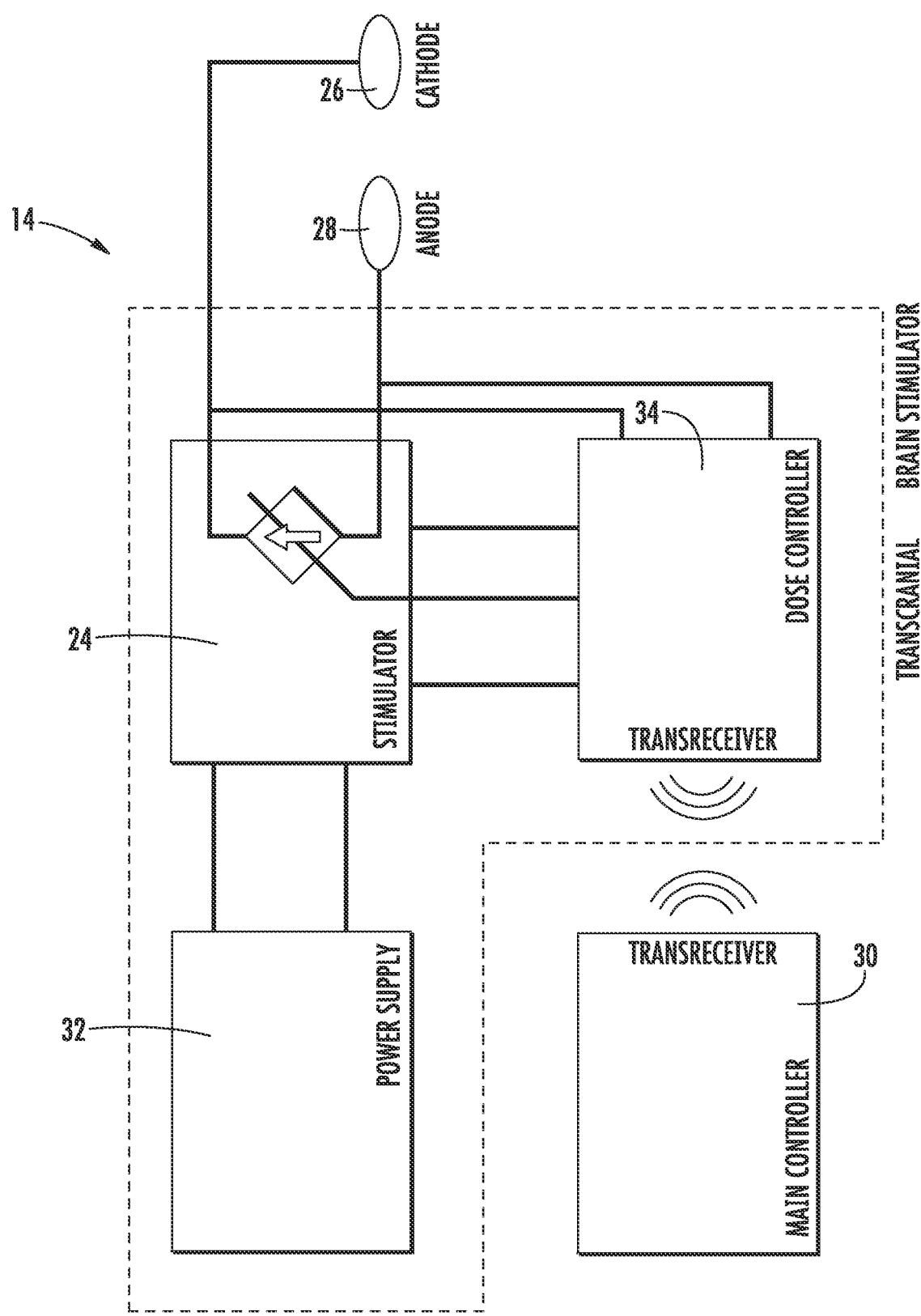
FIG. 4 illustrates a schematic diagram of a transcranial direct current stimulation component of the system, by focusing on the component implemented on the headband according to an embodiment of the present invention.

FIG. 4 illustrates a schematic diagram of a transcranial direct current stimulation component of the system, according to an embodiment of the present invention. In general, the transcranial direct current stimulation component is designed in such a way that it is easily implemented, for example in a headband that holds the two electrodes over the left and right motor cortices. In order to facilitate the use of the system, the stimulator and dose controller implemented to the headband in such a way that minimize the interaction with the subject. The device is powered by a re-chargeable battery and executes stimulation characteristics set by the external controller, which are transmitted wirelessly. The stimulation can also be monitored wirelessly. As illustrated in FIG. 4, the transcranial direct current stimulation component 14 includes a stimulator unit 24 having an anode 26 and a cathode 28. The stimulator unit 24 is coupled to a power source 32 that can be re-chargeable such as a battery. The stimulator unit 24 is also coupled to a dose controller 34 that is configured to transmit to and receive signals from a main controller unit 30. The main controller unit 30 can be programmed with information related to the stimulation pattern for the transcranial direct stimulation.

It should be noted that the controller 34, the main control unit 30 and the force controller 22 can all include a computing device such as a microprocessor, hard drive, solid state drive or any other suitable computing device known to or conceivable by one of skill in the art. The computing device can be programmed with a non-transitory computer readable medium that is programmed with steps to execute the different stimulation levels, patterns, and configurations, the force transduction, and the integration of the stimulation and force transduction components.

Any such computer application will be fixed on a non-transitory computer readable medium. It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

Figure 5:
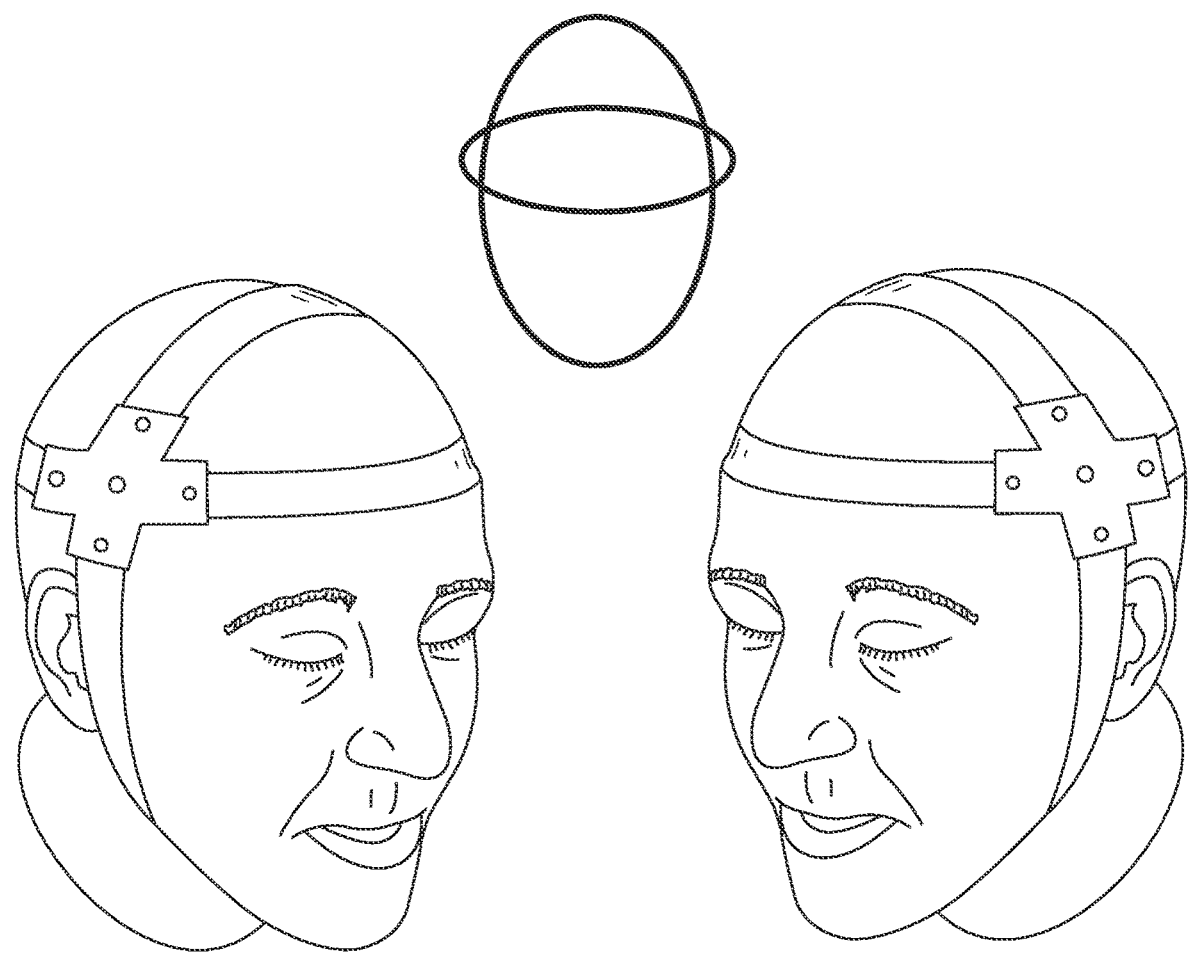
FIG. 5 illustrates a perspective view of electrode placement specific for Parkinson's disease, placed over the left and right primary motor cortex, according to an embodiment of the present invention.

FIG. 5 illustrates a perspective view of electrode placement specific for Parkinson's disease, according to an embodiment of the present invention. In accordance with the present invention, both motor cortices are simultaneously stimulated, with a pattern that depends on the laterality index measured during the behavioral task. This specific implementation of brain stimulator in the headband facilitated the process of localizing the motor cortex for any specific subject and reduced the need for the expert person in electrode placement. The headband was designed in such a way that it can be easily adjusted with respect to the head anatomy of any subject.

Figure 6:
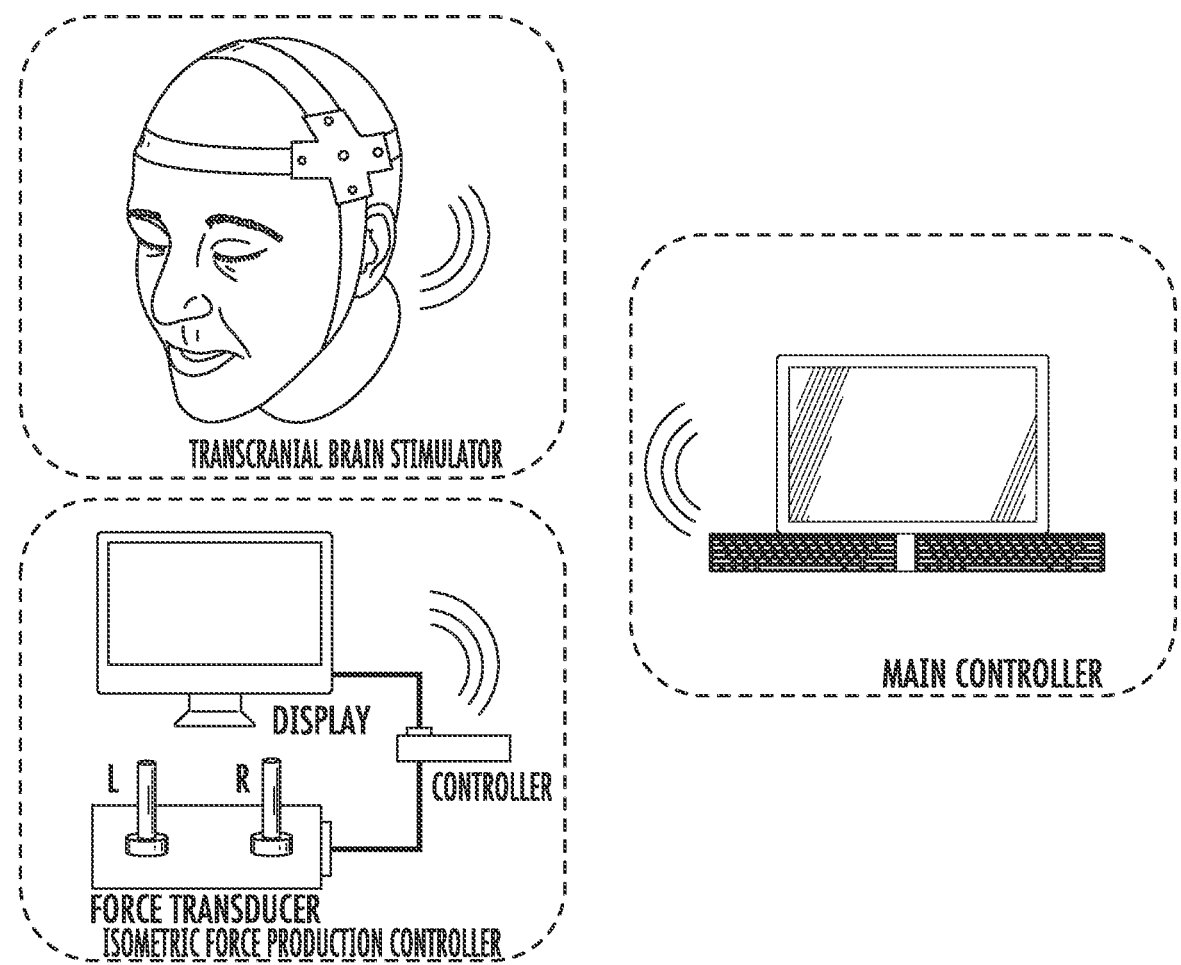
FIG. 6 illustrates a schematic diagram of the system consist of brain stimulator, behavioral task controller and main controller, according to an embodiment of the present invention.

FIG. 6 illustrates a schematic diagram of the system, according to an embodiment of the present invention. The transcranial direct current stimulation and isometric force production systems can each be subsystem designed individually and configured to communicate with each other via a main controller. This specific design integrated the behavioral task to the brain stimulation with minimum interaction. Each component functions independently and in a specific time manner which is set in the main controller.

Figure 7A:
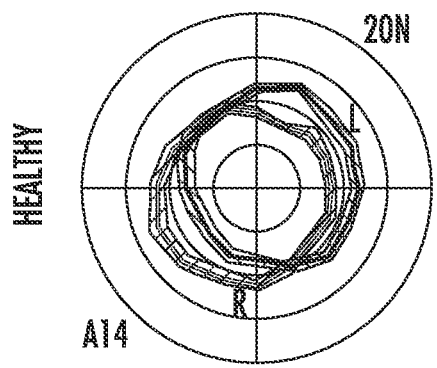
FIGS. 7A-7D illustrate schematic and graphical views of an exemplary force transduction exercise in one healthy individual and 3 PD affected individuals, all measured in a single session, and 2 PD affected individuals that were measured in 7 different sessions, all without stimulation, according to an embodiment of the present invention.
Figure 7B:
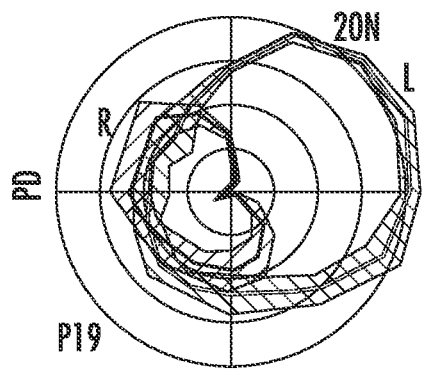
Figure 7C:
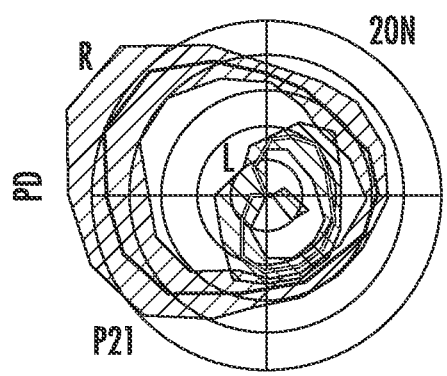
Figure 7D:
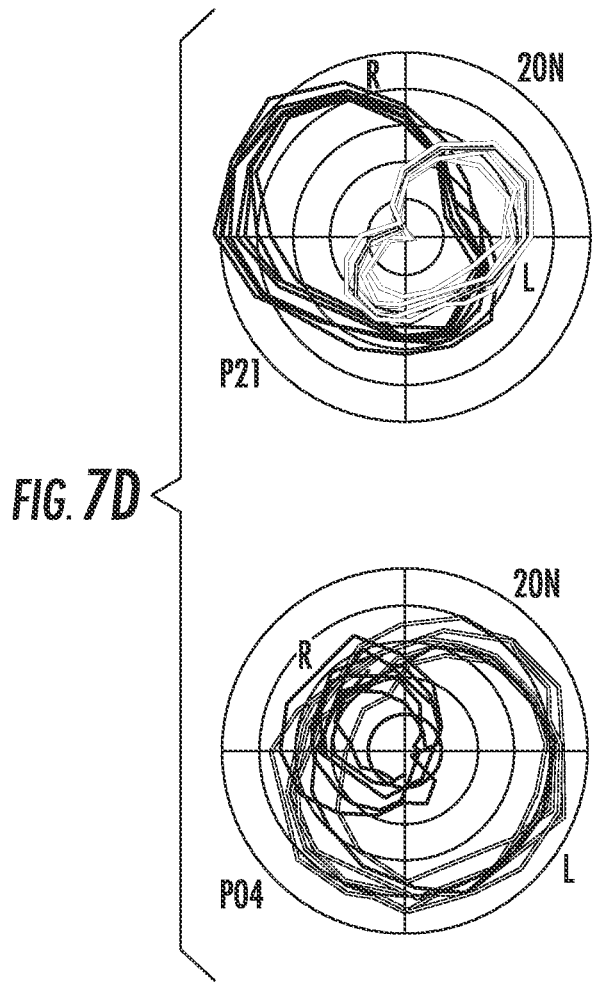

FIGS. 7A-7D illustrate schematic and graphical views of an exemplary force transduction exercise, according to an embodiment of the present invention. In the data illustrated here no stimulation is taking place. Rather, the measurements are being taken in order to determine the laterality index. The task is to produce forces with the two arms so that the sum of the two forces would be a vector that displaced a cursor to a target at 20N. The targets were randomly selected from 16 directions, uniformly distributed around a circle. FIG. 7A illustrates graphical data from a right-handed healthy elderly volunteer, displaying the forces produced by each arm in the task. For example, when given a target force of 20N at +45°, the volunteer chose to produce about 7N by the right arm and 13N by the left arm. FIG. 7B illustrates graphical data from a right-handed PD patient with a negative laterality index. FIG. 7C illustrates graphical data from a right-handed PD patient with a positive laterality index. In these figures, error-bars (shaded region) represent mean±1 SD as measured across 10 trials of a single session. FIG. 7D illustrates reproducibility of results. Two right-handed PD patients, one with a negative laterality index (bottom subplot), and the other with a positive laterality index (top subplot), were repeatedly measured in the bimanual task over the course of two months. Each line represents the measurement from a single session.

Figure 8A:
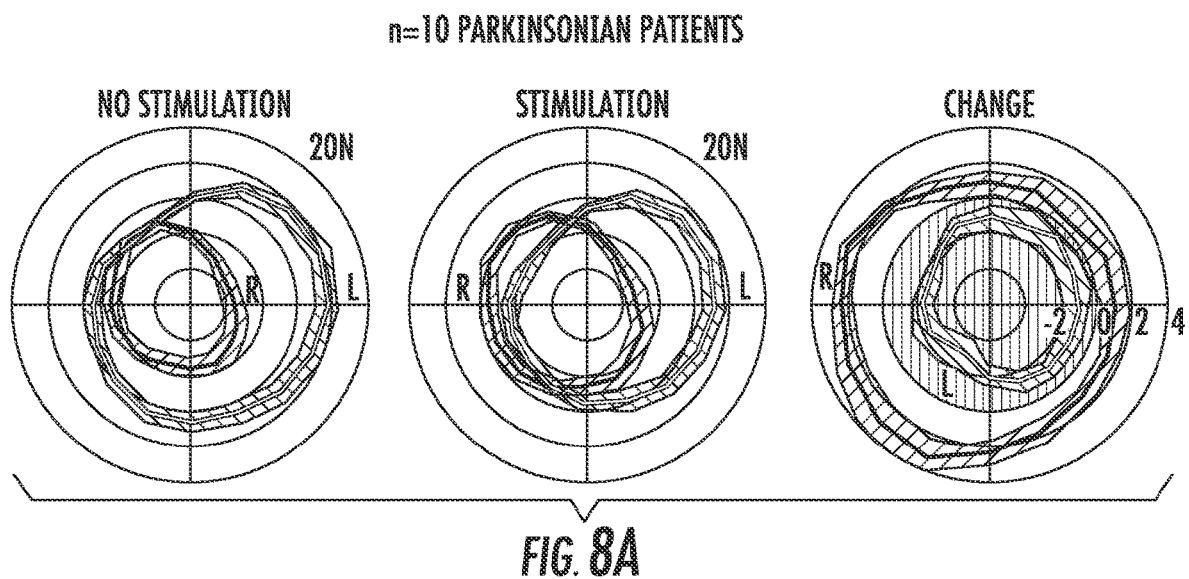
FIG. 8A-8C illustrate graphical views of the effect of transcranial direct current stimulation in 10 PD affected individuals, including the no-stimulation condition, the stimulation condition, and the change in force measurements, change in laterality index, and the clinical scores immediately before and immediately after stimulation, according to an embodiment of the present invention.
Figure 8B:
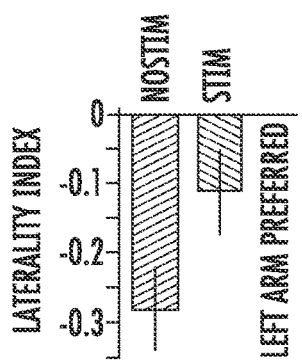
Figure 8C:
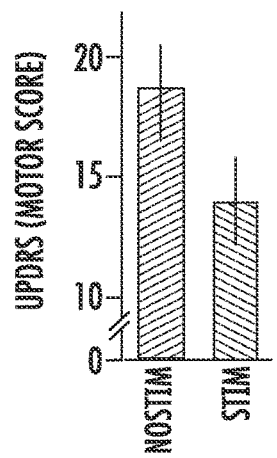

FIG. 8A-8C illustrate graphical views of the effect of transcranial direct current stimulation, according to an embodiment of the present invention. FIG. 8A illustrates effects of tDCS in 10 PD patients, all with negative laterality index. Force measurements are shown in a session without stimulation, in a session with +2 mA anodal stimulation of the right motor cortex (cathodal electrode placed on the right motor cortex), and the change in the force measurements across subject. Error bars are mean±1 standard error of the mean. FIG. 8B illustrates that the laterality index improved significantly from the no-stimulation to the stimulation condition. FIG. 8C demonstrates the clinical scores (UPDRS, motor) taken in the no-stimulation condition, and again in the stimulation condition. The motor symptoms, as measured by this clinical score, improved significantly.

FIGS. 9A-9D illustrate graphical views of results of a 10-day study, according to an embodiment of the present invention. Patients (n=8) participated in a 10 day study in which they received either no stimulation (control), sham stimulation (stimulator turned on and then immediately off), or real stimulation. FIG. 9A illustrates a graphical view of performance in the behavioral task. The top row illustrates data from a subject with negative laterality index, and the bottom row illustrates data from a subject with positive laterality index. Each line in each column of data represents measurements from a single day. FIG. 9B illustrates a graphical view of the contribution of the affected side increased on stimulation days. The affected side is labeled as the side that on average produces more force in the behavioral task. FIG. 9C illustrates a graphical view of the clinical scores taken during the study. The clinical scores are larger when the symptoms of the disease are worse. Stimulation reduced the clinical symptoms. FIG. 9D illustrates a graphical view of the self-rating that the participants provided at the start and end of the study. PDQ-39 is a commonly used clinical measure of quality of life. A smaller number indicates a better quality of life.

Figure 10A:
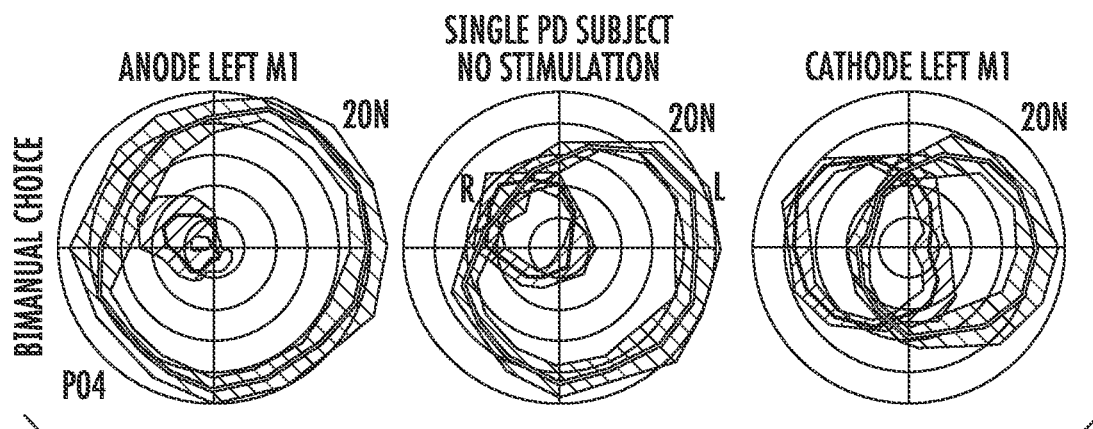
FIGS. 10A-10C illustrate graphical views of results of a pattern of stimulation that worsens symptoms of PD participants.
Figure 10B:
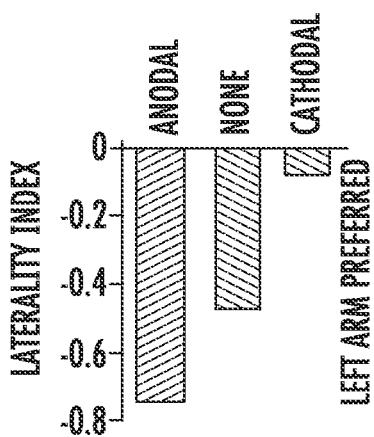
Figure 10C:
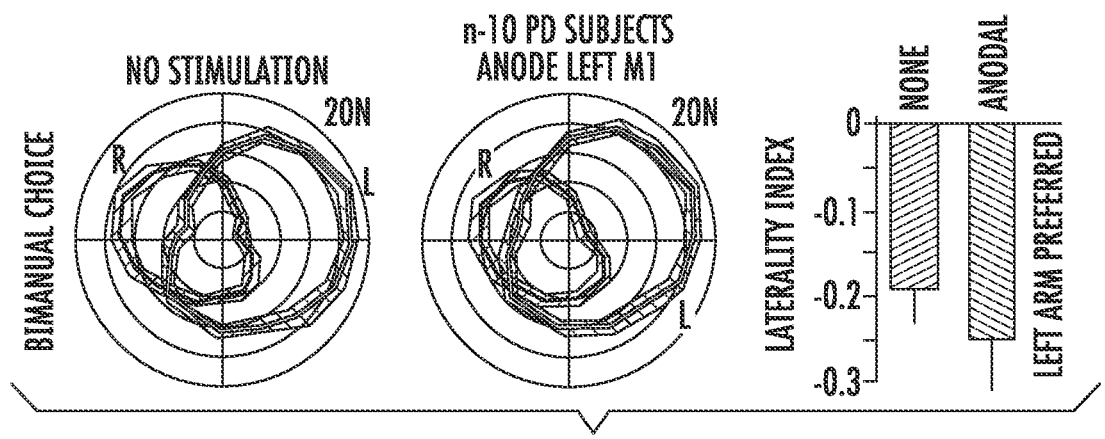

FIGS. 10A-10C illustrates graphical views of results of a pattern of stimulation that worsens symptoms of PD participants. FIG. 10A illustrate graphical views of force production in a single PD patient that was tested on 3 separate days with no stimulation, anodal stimulation of the left M1 (cathode on the right M1), and cathodal stimulation of the left M1 (anode on the left M1). The laterality index for this participant is negative. When the electrode on the left M1 receives anodal current, symptoms worsen. However, when the electrode on the left M1 receives cathodal current, symptoms improve. FIG. 10B illustrates graphical views of the laterality index in this patient. The index improved with cathodal stimulation of the left M1, and worsened with anodal stimulation. FIG. 10C illustrates graphical views the results of a study with 10 PD participants. All of these participants had a negative laterality index, as illustrated by the data from the force production task in the no-stimulation condition. When anodal stimulation was applied to the left M1, the laterality index worsened, becoming even more negative. Therefore, some forms of transcranial direct current stimulation can worsen symptoms of the patients.

All of the patients that were examined were on their normal schedule of medication. This is likely to have played an important role in the effects of tDCS. A key finding has been regarding the interaction of tDCS and basal levels of dopamine. In healthy individuals, anodal tDCS of M1 makes the neurons easier to excite, as it brings them closer to depolarization threshold. However, when healthy people are given L-dopa to increase basal levels of dopamine, the effects of anodal tDCS are blunted, eliminating the potentiation. That is, in healthy people increased basal levels of dopamine make anodal tDCS ineffective in potentiating the cortical neurons. This interaction of anodal stimulation with basal levels of dopamine may explain why positive effects of anodal tDCS have not been seen in medicated patients.

In a recent rodent study, following 10 min of cathodal tDCS of the frontal lobe, there was 60% increase in dopamine concentrations in the ipsilateral striatum, an increase that was sustained for hours after cessation of cortical stimulation. Importantly, this increase was specific to cathodal stimulation, as anodal stimulation produced 10% decrease in dopamine. In contrast, neither cathodal nor anodal stimulation affected concentrations of serotonin in the striatum. Therefore, it is possible that cathodal stimulation of human M1 indirectly enhanced dopamine release in the ipsilateral striatum. However, the key question is which motor cortex should be the anode, and which should the cathode. In our experimental work, a behavioral task has been established the uses force production to identify the stimulation pattern for each hemisphere. It is plausible, however, that the mechanism of action of tDCS effect on parkinsonism in humans is more complex than simply modulating striatal dopamine levels, as with appropriate application of tDCS it may be possible to produce motor benefits even when their dopamine levels are optimized with adequate pharmacotherapy.

While there are tDCS devices sold for other uses, particularly gaming, these devices typically place one electrode over the left motor cortex and the other over the right forehead. The results illustrated in FIGS. 10A-10C suggest that this form of stimulation not only is ineffective, it actually worsens the symptoms of the disease in the presence of PD medication. The novelty of the present invention is in the specific locations of the brain that are stimulated, and the pattern of stimulation. One electrode is placed over the right motor cortex, and the other electrode is placed over the left motor cortex. In PD patients that have a negative laterality index, anodal stimulation is applied over the right motor cortex, and cathodal stimulation over the left motor cortex. In PD patients that have a positive laterality index, anodal stimulation is used over the left motor cortex, and cathodal stimulation over the right motor cortex. Whereas this specific form of stimulation is effective in improving symptoms, other forms of stimulation can lead to worsening of symptoms. A second component of the present invention is to couple the stimulation with a behavioral task that attempts to engage cortical plasticity to increase the neuronal pool size available for control of the contralateral limb.

In an exemplary experiment, a bimanual task was given in which people chose how much force to produce with each arm so that the sum would equal a target. As expected, right-side affected patients (n=15) preferred to produce force with their less affected side. However, this preference was direction dependent: for some directions the patients preferred the affected arm. This demonstrated that contrary to the current view, cost of force production was not globally higher on the affected side. Signal-dependent noise was measured in each arm and all directions and found that the preferences in the bimanual task were well explained by the unimanual noise patterns: the reluctance to produce force was present only for directions for which noise on the affected side was higher than the unaffected side. These noise patterns are a reflection of the size of neuronal pools available for control of the limb in the motor cortex. To alter the noise, transcranial direct current stimulation was applied. Anodal stimulation worsened noise, and also worsened the motor symptoms. However, cathodal stimulation in n=10 PD patients improved unimanual noise, preferences for force production, and UPDRS motor symptoms. This 1-day study was followed with a 10-day study of n=8 patients and observed robust improvements in symptoms with actual stimulation as compared to sham stimulation.

In the experiments, it was demonstrated that effort cost is not globally higher on the affected side, but is direction-dependent in a pattern that is well explained by signal-dependent noise. This noise was altered using 5-days of repeated tDCS, resulting in 25% reduction in motor UPDRS. Based on the data it was concluded that through specifically applied long-term tDCS and focused motor rehabilitation it may be possible to produce lasting improvement of motor functions in Parkinson disease.

Another experiment including an isometric task in which people held two force transducers, one in each hand, was also conducted. The goal was to use the left and right arms in such a way as to produce a target force vector, indicated by a cursor. The position of the cursor was the sum of the force produced by each arm. For each target the subjects chose how much force to produce with each arm. This choice was direction dependent, but remarkably consistent over repeated days.

Figure 11:
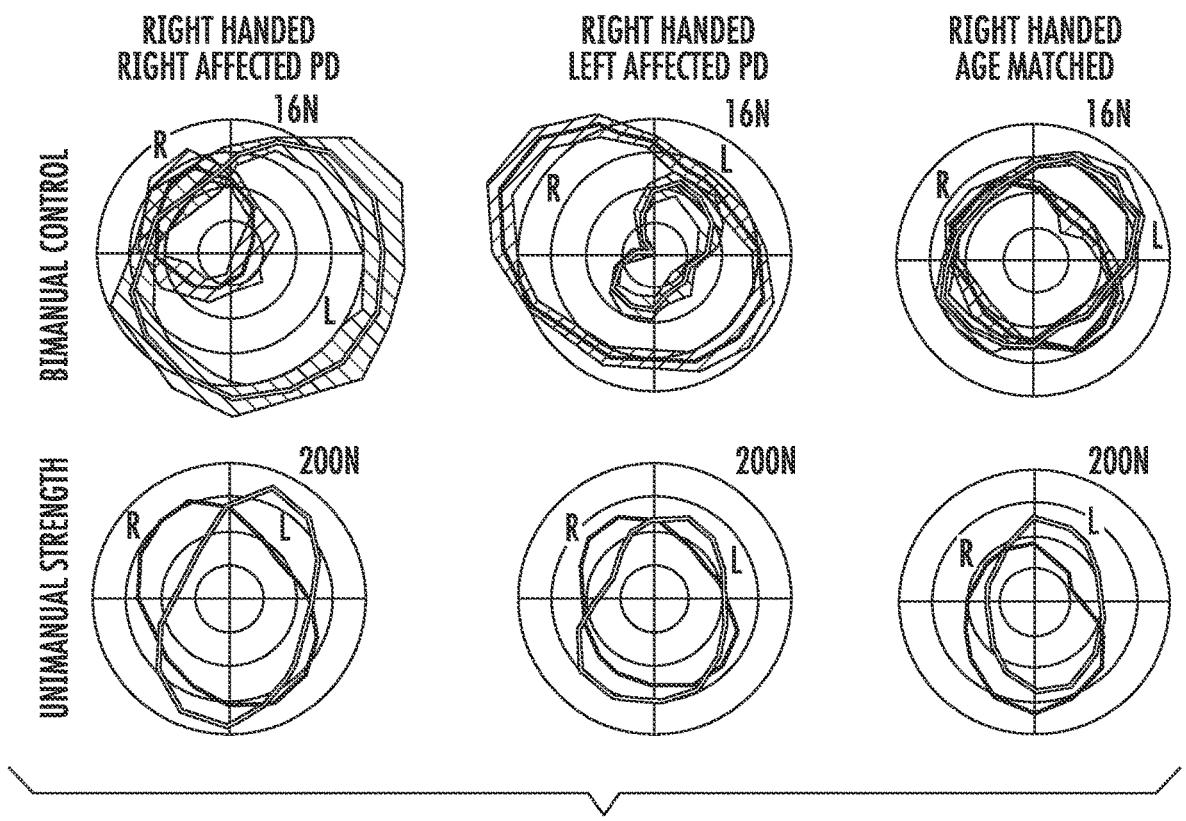
FIG. 11 illustrates graphical views representing PD affected bimanual choice on the affected side.

FIG. 11 illustrates graphical views representing PD affected bimanual choice on the affected side. The graphs show bimanual control and unimanual strength for right handed, right affected PD; right handed, left affected PD; and right handed, age matched subjects.

Figure 12:
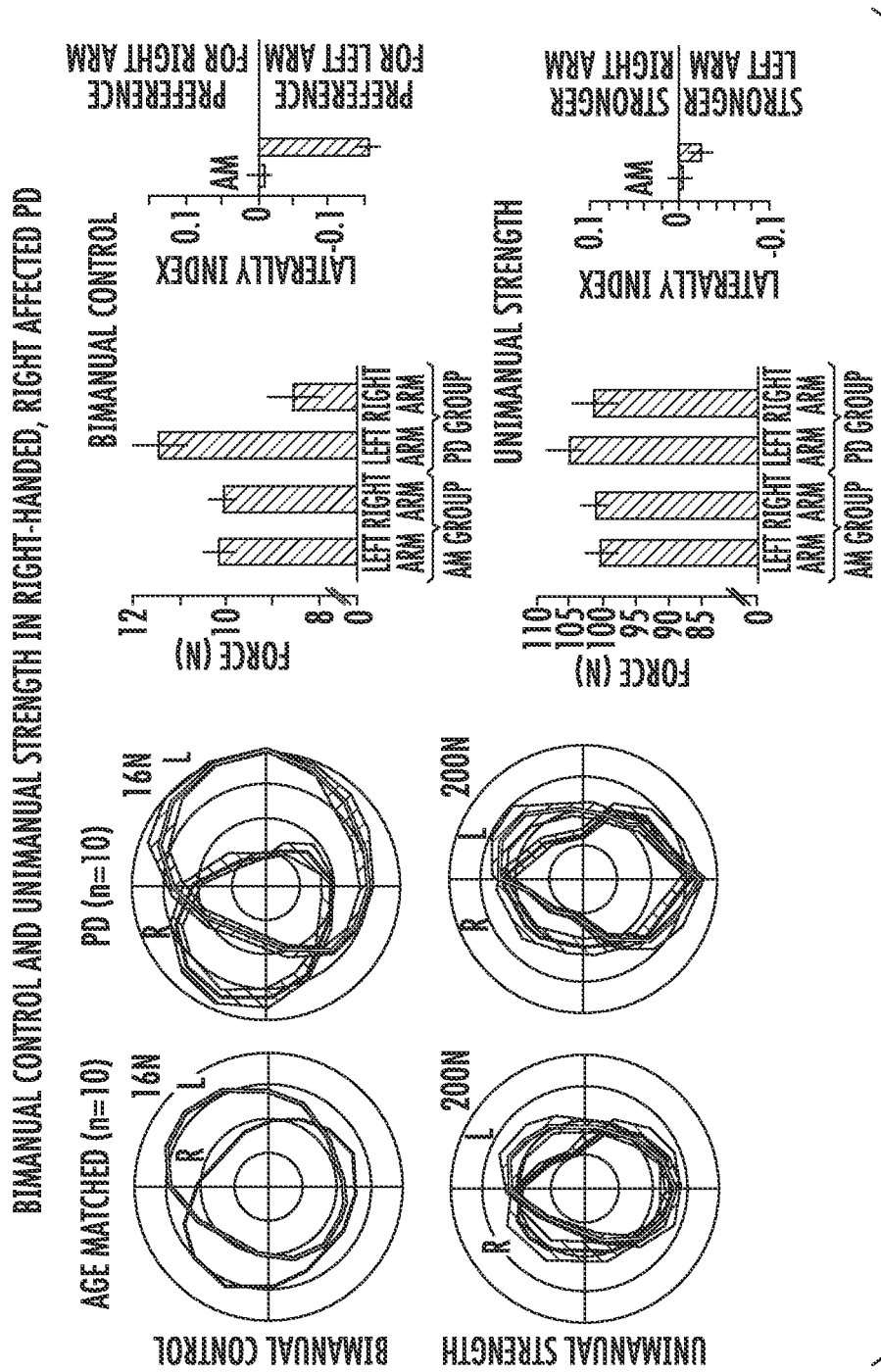
FIG. 12 illustrates graphical views representing bimanual control and unimanual strength in right-handed, right affected PD subjects.

FIG. 12 illustrates graphical views representing bimanual control and unimanual strength in right-handed, right affected PD subjects. Age matched subjects are also included as a control group. The bar graphs on the right show force (N) and laterality index for bimanual control and unimanual strength for both the PD subjects and the control group.

Figure 13:
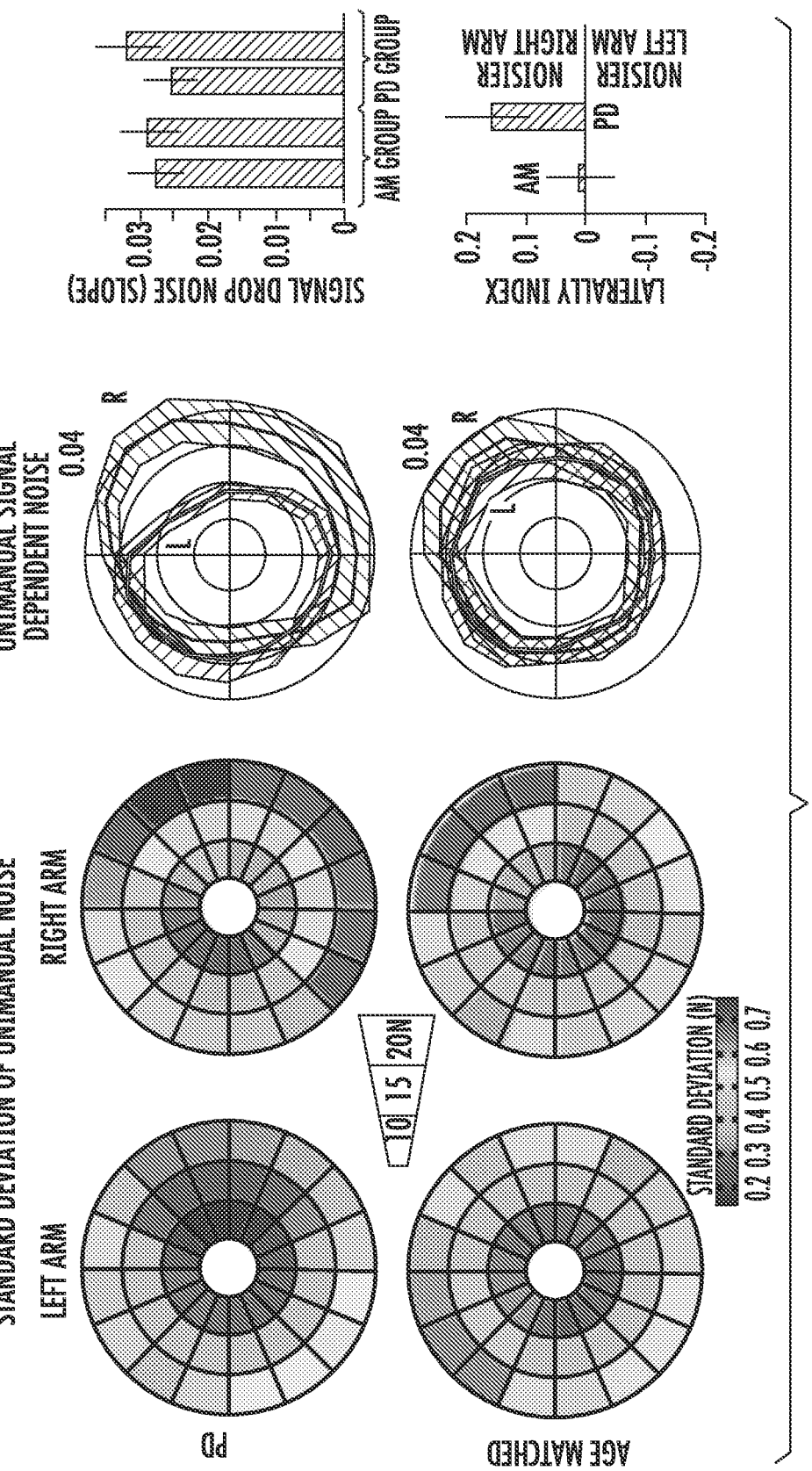
FIG. 13 illustrates graphical views showing that signal-dependent noise was lateralized in PD subjects but not in control subjects.

FIG. 13 illustrates graphical views showing that signal-dependent noise was lateralized in PD subjects but not in control subjects. In an isometric unimanual task, the standard deviation of force as a function of force in various directions was measured and the slope of the relationship was computed. The left graphs show standard deviation of unimanual noise for the PD subjects and the control group. The middle graphs show unimanual signal dependent noise for the PD subjects and the control group, and the right graphs show the slope for the PD subjects and the control group as well as the laterality index for the PD subjects and the control group.

Figure 14:
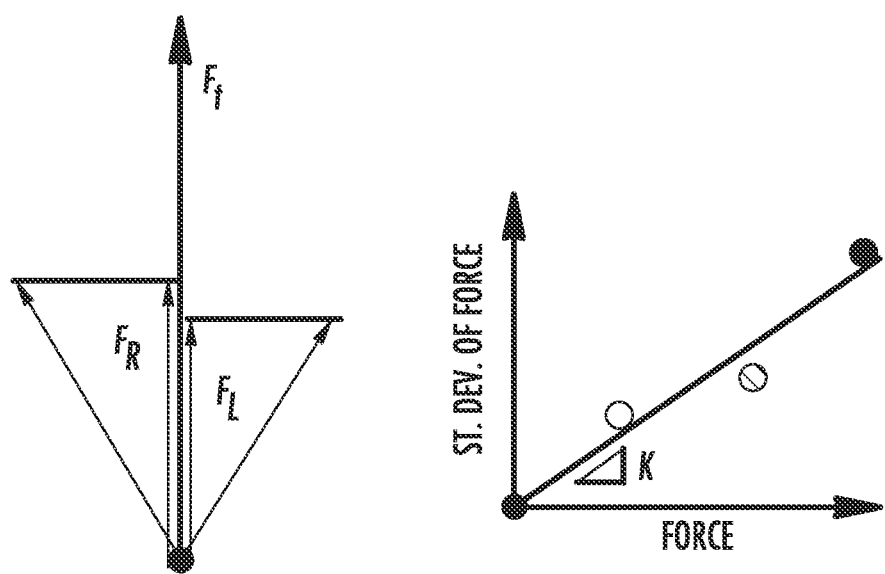
FIG. 14 illustrates graphical views representative of a candidate cost function and a framework for signal dependent noise.

FIG. 14 illustrates graphical views representative of a candidate cost function and a framework for signal dependent noise. The candidate cost function is $$J = \{\text{var}[F_T]\} + \frac{1}{2}U^T U$$

and the framework for signal dependent noise is $$F_L = U_L(1+K_L\phi)$$

$$F_R = U_R(1+K_R\phi) \quad \phi \sim \mathbb{N}(0,1).$$

Figure 15:
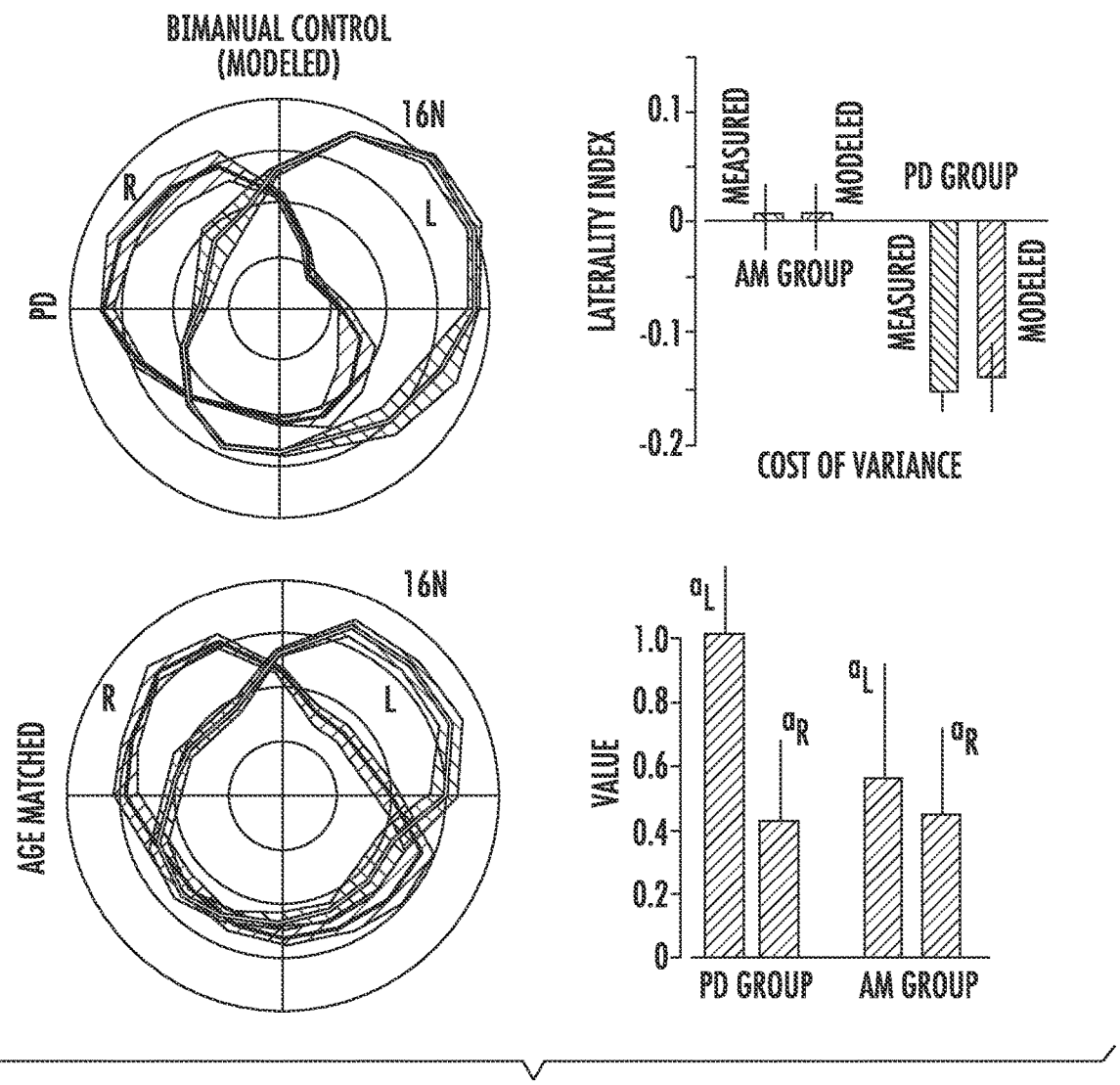
FIG. 15 illustrates graphical views that show that signal dependent noise in the unimanual task accounted for choice in the bimanual task in both the PD subjects and the control group.

FIG. 15 illustrates graphical views that show that signal dependent noise in the unimanual task accounted for choice in the bimanual task in both the PD subjects and the control group. The signal dependent noise of each arm for each direction was used to predict the choices that the subject makes in the bimanual task in all directions.

$$J = \frac{1}{2tr(K)}U^T AKU + \frac{1}{2tr(M)}U^T(I-A)MU$$

$$U = \frac{1}{U_L + U_R}\begin{bmatrix} U_L \\ U_R \end{bmatrix}$$

$$K = \begin{bmatrix} K_L^2 & 0 \\ 0 & K_R^2 \end{bmatrix}$$

$$A = \begin{bmatrix} \alpha & 0 \\ 0 & \alpha \end{bmatrix}$$

$$M = \begin{bmatrix} \dfrac{1}{MVF_L^2} & 0 \\ 0 & \dfrac{1}{MVF_R^2} \end{bmatrix}$$

For each subject, the unimanual strength and signal dependent noise were used to model contribution of each arm during bimanual control using the equations above.

Figure 16:
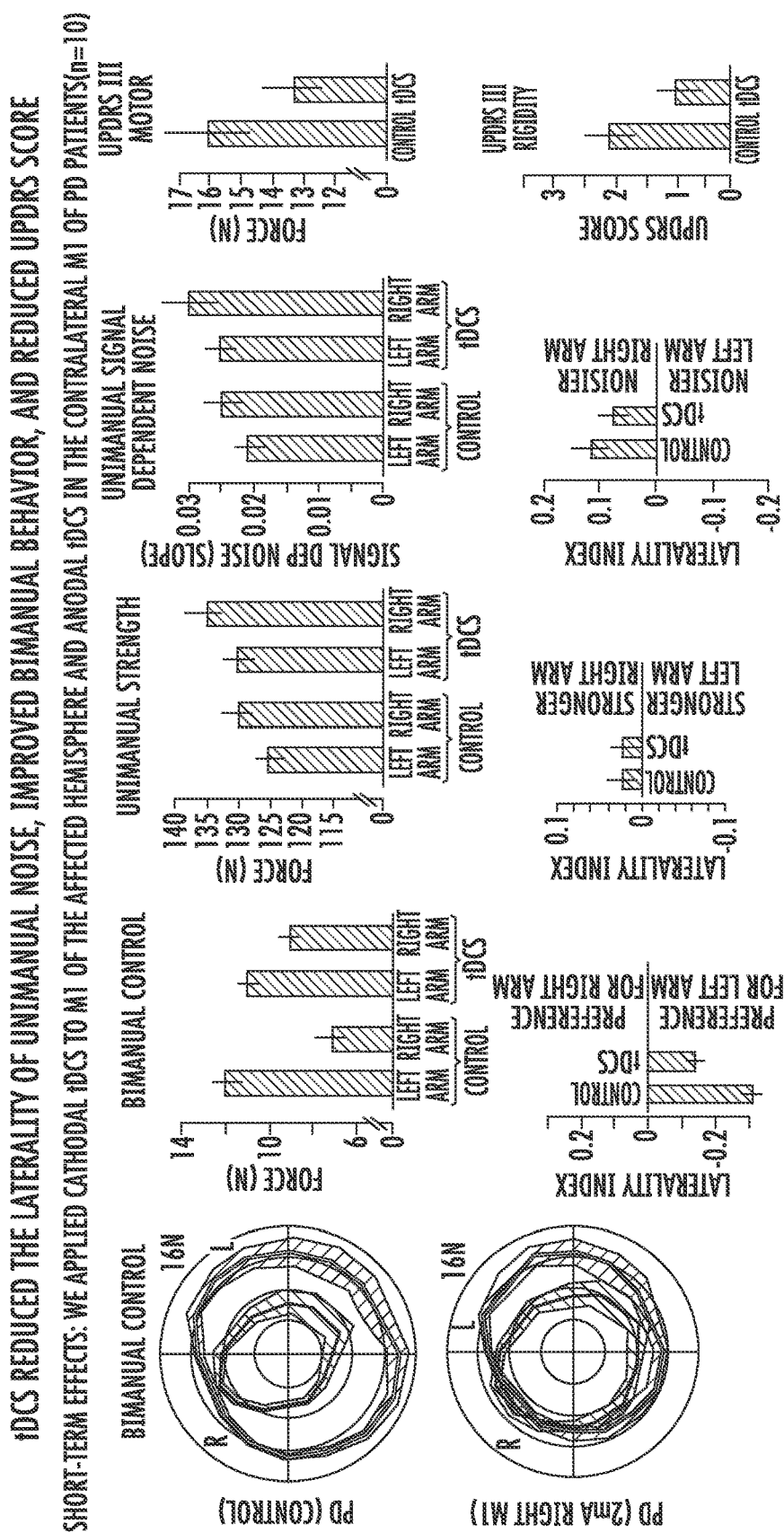
FIG. 16 illustrates graphical views that show that tDCS reduced the laterality of unimanual noise, improved bimanual behavior, and reduced the UPDRS score.

FIG. 16 illustrates graphical views that show that tDCS reduced the laterality of unimanual noise, improved bimanual behavior, and reduced the UPDRS score. These graphs show short term effects of applying cathodal tDCS to M1 of the affected hemisphere and anodal tDCS in the contralateral M1 of PD patients (n=10).

Figure 17:
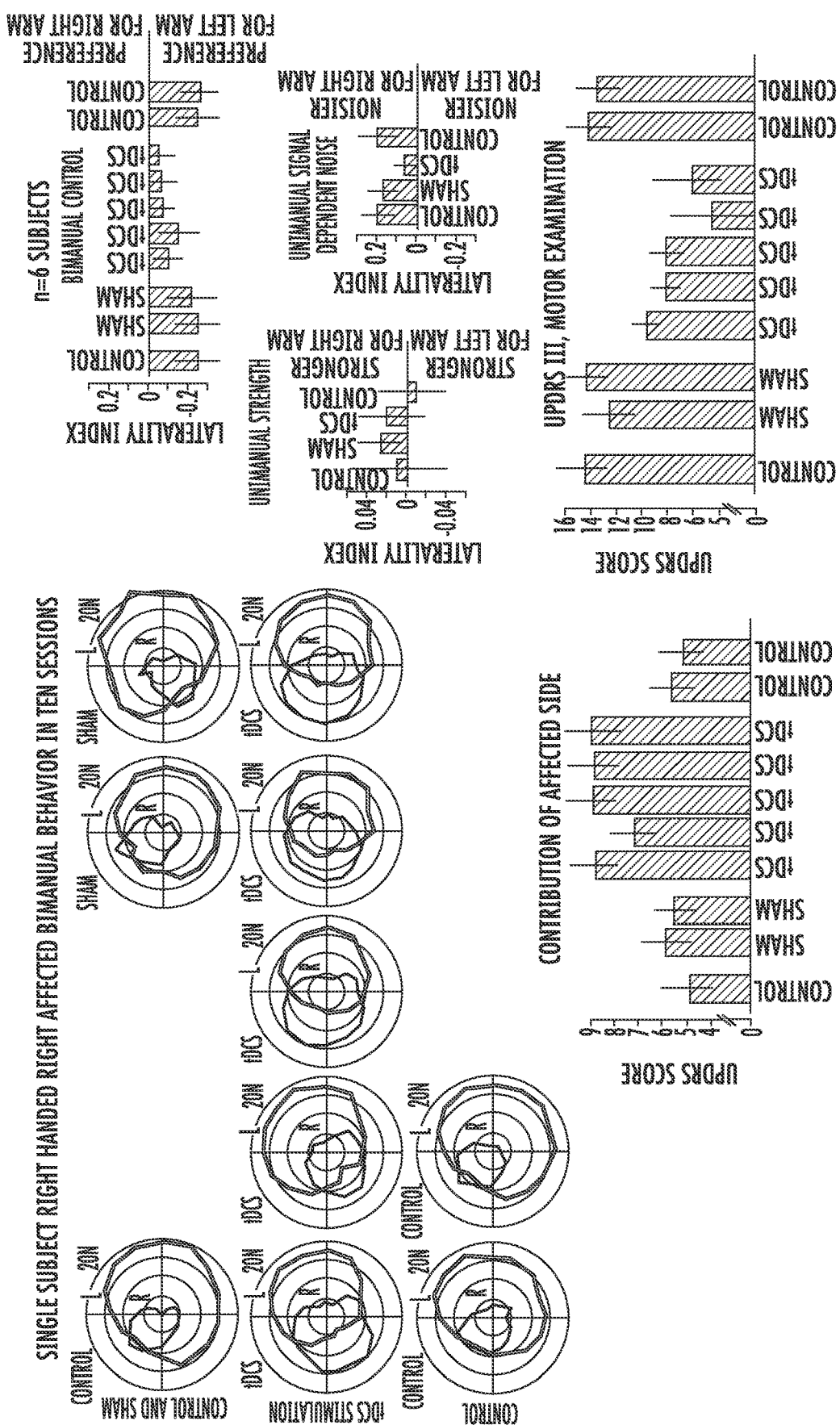
FIG. 17 illustrates graphical views of the long term effects of tDCS treatment.

FIG. 17 illustrates graphical views of the long term effects of tDCS treatment. Patients (n=6) participated in a 10 day study of tDCS. Cathodal tDCS was applied to M1 of the affected hemisphere and anodal tDCS to the contralateral M1. This produced an immediate reduction in laterality index of variance on the unimanual task. Consistent with this, the patients altered the choices that they made in the bimanual task: cathodal tDCS made their choices more similar to the healthy control subjects. The results of applying tDCS in multi-session experiments showed marked reduction in the motor subcore of the UPDRS. Motor choices PD patients make are due to a cost analysis that has two components: variance and effort. On the affected side, variance is significantly increased with respect to controls and the choices of PD patients are generally consistent with this increased variance. Unimanual variance of the PD patients is improved using tDCS. This produces an immediate improvement in their actions in bimanual tasks. The repeated session applications of tDCS improves motor symptoms of PD by decreasing UPDRS and may be of therapeutic relevance.

Another embodiment in accordance with the present invention is directed to a system and device for applying electric current transcranially to the brain via an implantable electrode. The system and device is designed to improve motor symptoms in Parkinson's disease (PD) and for treatment of a number of other disease indications, such as depression and movement disorders. In a unique implantable design, according to an embodiment of the present invention, a tDCS brain stimulation system is implemented in two separate parts. The system includes a subcutaneously implantable electrode with a driver and a main controller. The system of the present invention also includes electrode placement and stimulation technique specifically targeted for PD and movement disorders.

The present invention implements tDCS stimulation techniques specifically designed for PD patients and other movement disorders to minimizing the interaction and inconvenience to the patient with respect to electrode placement, setting stimulation parameters, reducing total electric power apply to the brain, and providing long term brain stimulation therapy. Technology today allows for the medical device to be wirelessly powered and even communicate with a power source at the same time over distance and through materials such as plastic and human tissue. Using this technique, systems can be designed to transfer power and data over distance safely and efficiently. The technology has the potential to enable a new generation of implantable brain stimulators, specifically consisting of extracranial implantable electrodes for transcranial brain stimulation. It may facilitate the use of brain stimulation as a treatment for PD and other movement disorders in terms of electrode placement and does control for long term use.

Other advantage of implantable stimulation device is reduction of total power in stimulation process by eliminating the dissipated power in the skin. Some simulation based studies show the change in current density magnitudes variation throughout the tissues and step jumps in the current density occurred at each tissue boundary. The largest current density magnitude was located on the skin surface. By implanting the stimulation electrodes under the skin, the total current will be dramatically reduced for having the same effect on the cortical area, which is very important for long term use of stimulator.

Figure 18:
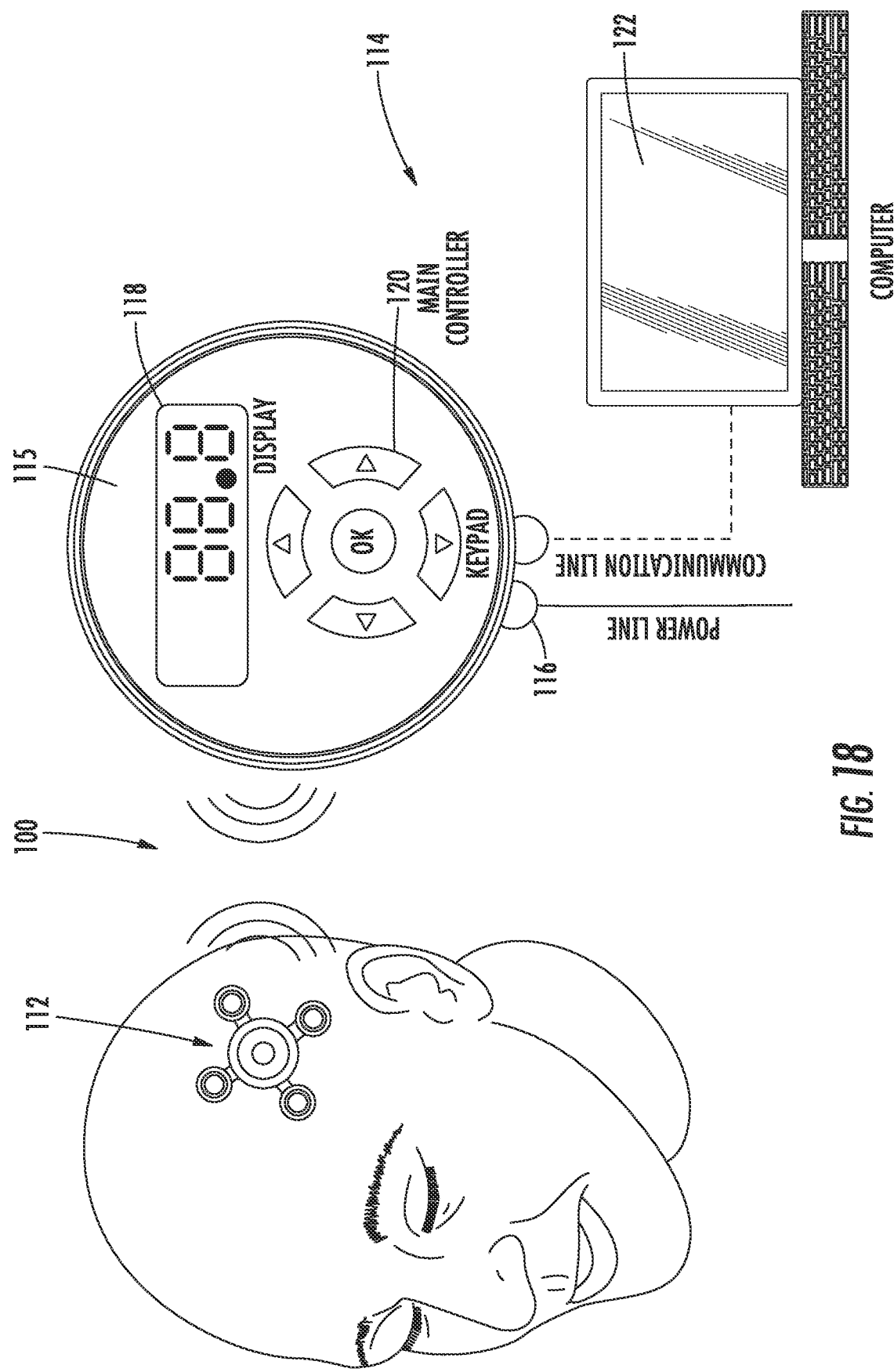
FIG. 18 illustrates a schematic diagram of system for delivery of transcranial current stimulation through an implanted electrode subcutaneously under the scalp skin which receives power wirelessly from an outside controller, according to an embodiment of the present invention.

FIG. 18 illustrates a schematic diagram of system for delivery of transcranial direct current stimulation subcutaneously, according to an embodiment of the present invention. As illustrated in FIG. 18, the system 100 includes a implantable component 112 and an external main component 114. The implantable component 112 includes anodal and cathodal electrodes, a transcranial direct current stimulation driver, and a wireless power and data transmission line. The implantable component 112 will also be described in further detail herein. The main external component 114 includes a controller 115, an input power interface 116, a display 118 and keyboard 120 for a user interface and monitoring, a wireless power transmission system, a data send and receive module in a specific manner for wireless power and dose control, and a standard interface with an external computer 122 or other controllers for advance does control monitor and data logging. The external main controller will also be described further herein.

Figure 19:
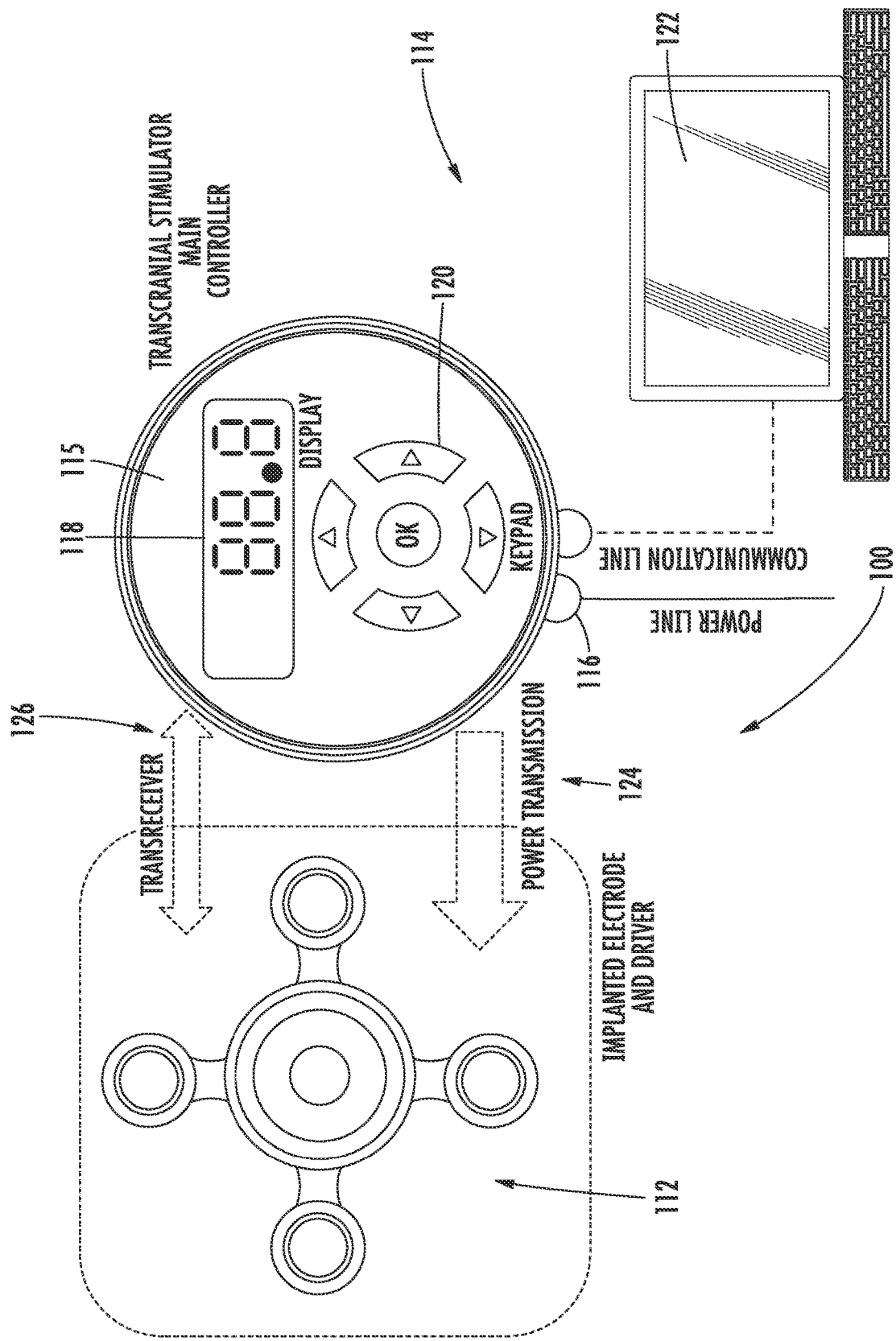
FIG. 19 illustrates a schematic diagram of the main components of the system for delivery of transcranial current stimulation, according to an embodiment of the present invention.

FIG. 19 illustrates a schematic diagram of the main components of the system, the implantable component and the main external component, and how they are related to each other. FIG. 19 illustrates that the subcutaneous implantable component 112 receives power thought the wireless power transmission line 124 from the external main component 114 and also communicates wirelessly via a transceiver 126 with it, according to an embodiment of the present invention.

Figure 20:
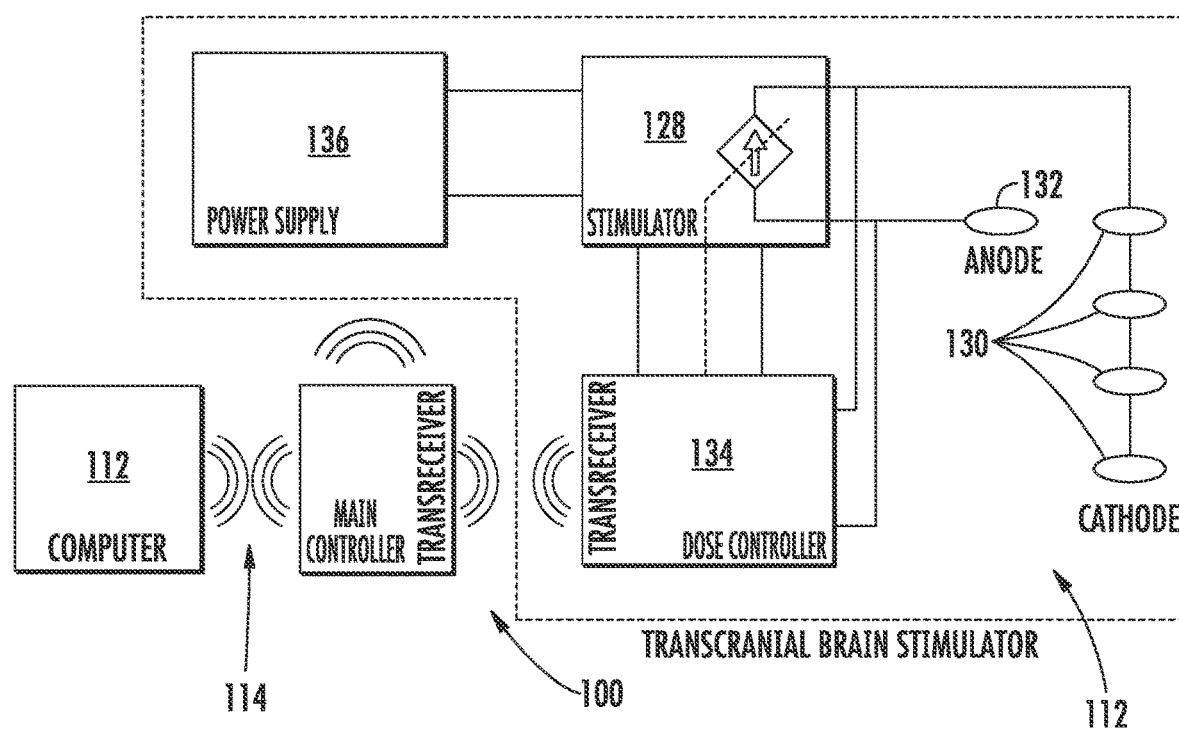
FIG. 20 illustrates a functional block diagram of the main component of the system for delivery of transcranial current stimulation, according to an embodiment of the present invention.

FIG. 20 illustrates a schematic diagram of a transcranial direct current stimulation function of the implantable component and its communication with the external main component, according to an embodiment of the present invention. In general, the transcranial direct current stimulation implantable function of the implantable component 112 is designed in such a way that it is implemented subcutaneously and includes electrodes, stimulator, power supply, and a dose controller. More particularly, the implantable component 112 includes a cathode 130 and an anode 132. The stimulator 128 is triggered by the dose controller 134 and power is provided to the stimulator 128 via the power supply 136. The external main component 114 is used to control the dose controller 134 using the transceivers in the external main controller 114 and the dose controller 134.

The stimulation electrodes designed in high-definition transcranial direct current stimulation montage allows precise targeting of cortical structures. The region of current flow is mostly distributed by the area of the 4×1 ring, such that decreasing ring radius increased focality. High-definition transcranial direct current stimulation montage allows for unifocal stimulation, meaning the polarity of the center electrode will determine the direction of neuromodulation under the ring. This is in contrast to conventional tDCS where the need for one anode and one cathode always produces bidirectional modulation. 4×1 HD-tDCS thus provides the ability not only to select a cortical brain region to target, but to modulate the excitability of that brain region with a designed polarity without having to consider return counter-electrode flow.

Figure 21:
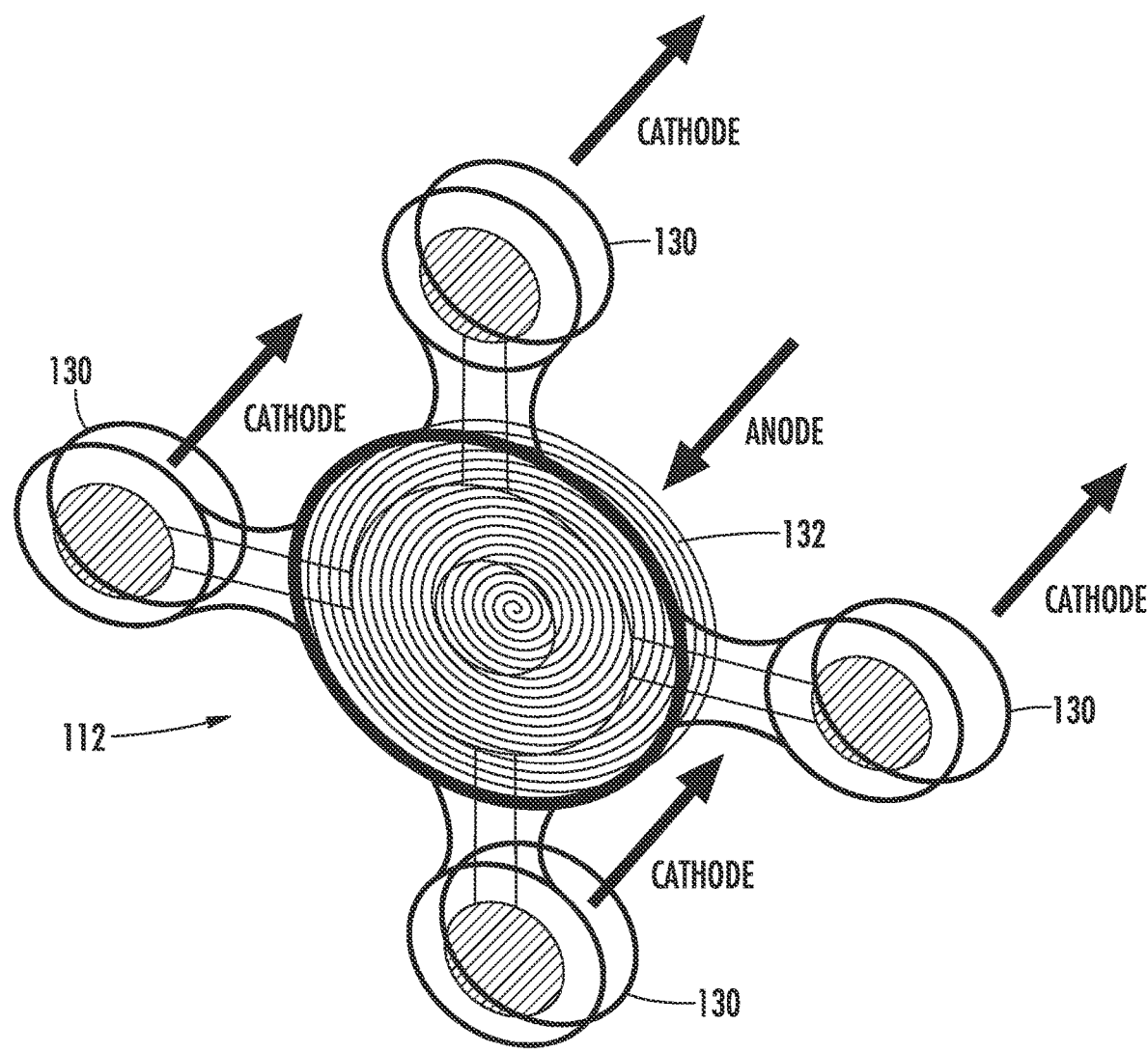
FIG. 21 illustrates a schematic diagram of an implantable electrode for transcranial current stimulation component of the system, according to an embodiment of the present invention.

FIG. 21 illustrates a schematic diagram of the implantable component of the tDCS, according to an embodiment of the present invention. FIG. 21 illustrates the implantable component 112 and an exemplary orientation of the cathodes 130 and the anode 132 in a ring like shape for providing a radius of stimulation treatment. It shows the placement of the power receiving coil which is used as a data communication channel as well. The arrangement of electrodes is in such a way that it could provide either very focal anodal stimulation or cathodal stimulation. The stimulator driving current source and the dose control are emended to the stimulating electrode. While four cathodes 130 and one anode 132 are illustrated in FIG. 21 any suitable number and configuration of cathodes and anodes known to or conceivable by one of skill in the art could also be used.

Figure 22:
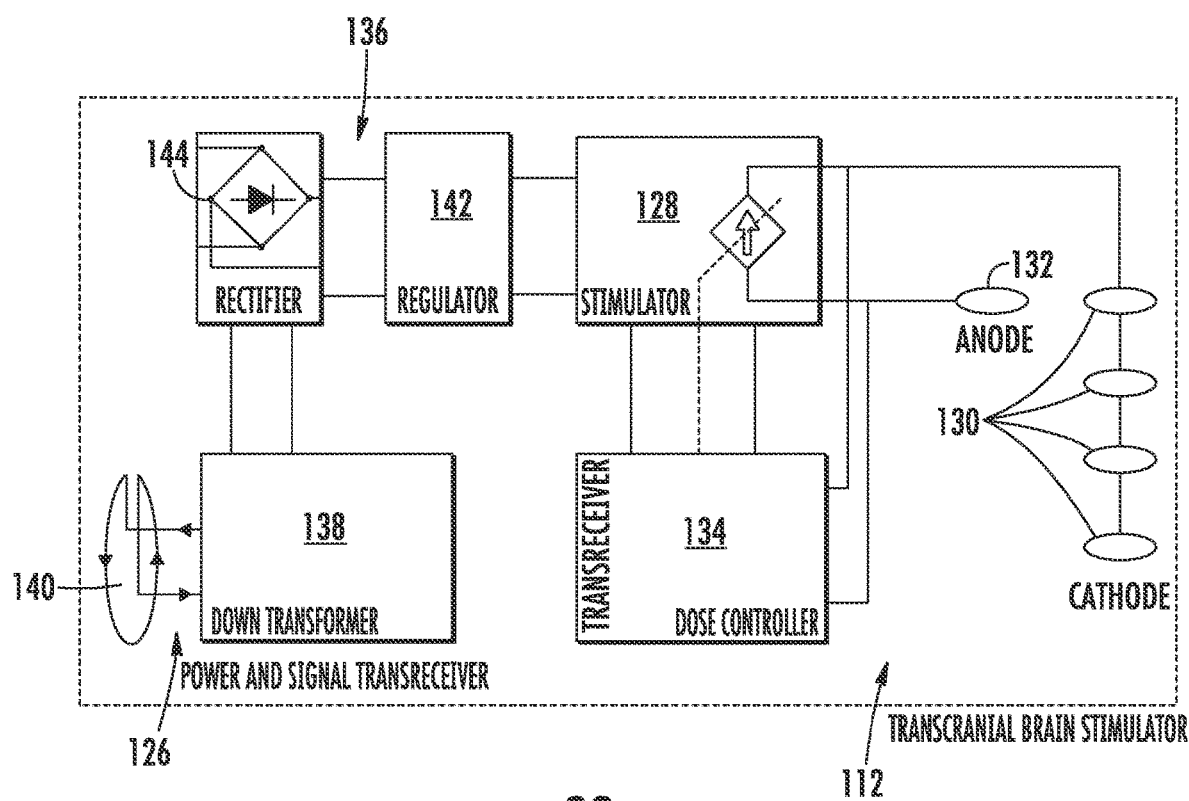
FIG. 22 illustrates a functional block diagram of an implantable electrode for transcranial current stimulation component of the system, according to an embodiment of the present invention.

FIG. 22 illustrates a schematic diagram of the implantable component of tDCS, according to an embodiment of the present invention. The implantable component includes, wireless power and data transmission, power regulator, stimulation current driver, dose control and stimulation electrodes.

Figure 23:
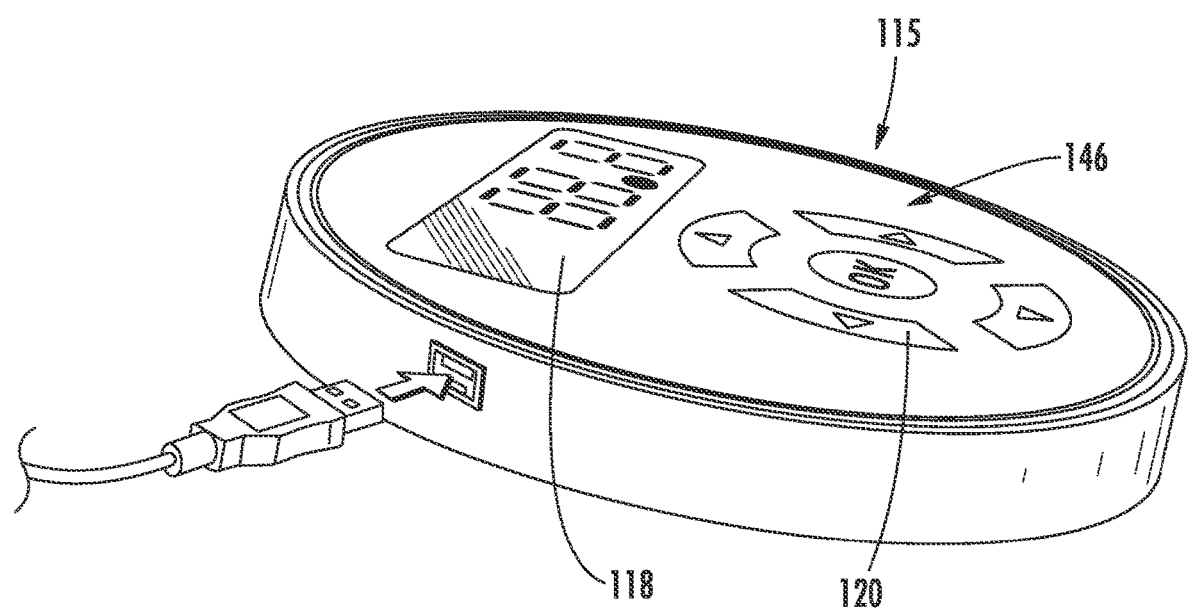
FIG. 23 illustrates a schematic diagram of an external controller for providing power wirelessly via an inductive channel and also handshaking from the same channel, according to an embodiment of the present invention.

FIG. 23 illustrates a schematic diagram of the external controller 115 for providing power wirelessly via an inductive channel and also handshaking from the same channel, according to an embodiment of the present invention. The basic function of the external controller 115 is to emit wireless power into space. Further functions may include regulating the transferred power level to ensure that recovered power is stable, adaptively changing the operating frequency so that the coupling efficiency is optimized. The external controller can be worn on human body, or placed in a room as a location fixed equipment. A user interface 146 with display 118 and keypad 120 is provided to set the parameters and also to monitor the current state of the device regarding does level and duration. More importantly it logs the state of the wireless power and communication channel and transmits them to the external computer.

Figure 24:
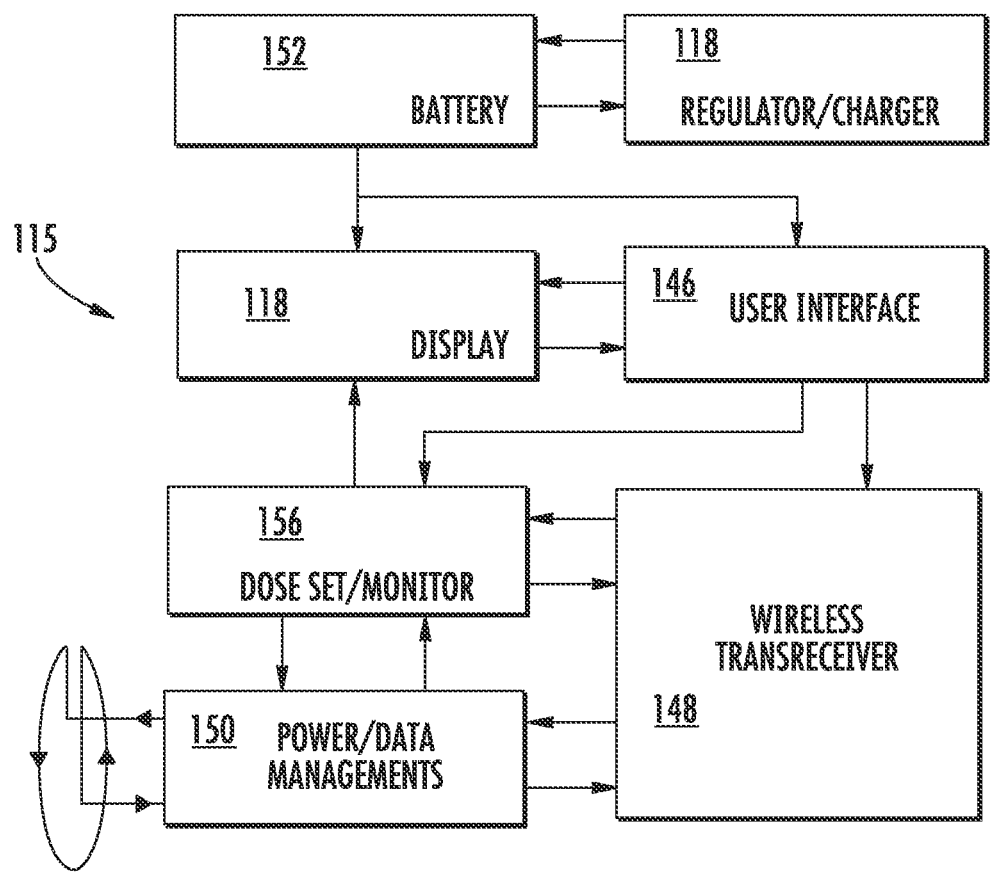
FIG. 24 illustrates a functional block diagram of the external controller for providing power wirelessly via inductive channel and also handshaking from the same channel, according to an embodiment of the present invention.

FIG. 24 illustrates a functional block diagram of the external controller for providing power wirelessly and interfacing with the user and external computer, according to an embodiment of the present invention. The transmitter 148 is composed of a primary power antenna, a DC-AC converter, a DC-DC converter, and a power management circuit 150. The DC energy source of the transmitter can be a group of batteries or a city power adapter. The DC-DC converter is responsible to convert the DC energy source to another designed DC voltage for the DC-AC converters and the power management circuits. The DC-DC converter can be fulfilled by linear regulators or switch-mode DC-DC converters. The DC-AC converter is the main component of the wireless power transmitter. It converts DC energy to AC energy at a specified operating frequency. The power efficiency of the transmitting side is essentially decided by the efficiency of the DC-AC converter. The power management circuit 150 is used to control the whole transmitter. Typical task includes adjusting the operating frequency and the transferred power level. It may also have wireless data connectivity with the power receiver. The data connectivity of element 150 can be used to send command to the receiver. It can be also designed to feedback power information from the receiver to the transmitter, so a close-loop power control can be set up. As FIG. 24 shows the external controller is battery 152 powered and the regulator 154 charges the battery. A keyboard 120 and a display 118 are the user interface 46 components. Any setting parameters are entered by the keyboard or could be set by the external computer. They also could be monitor by the small display.

Figure 25:
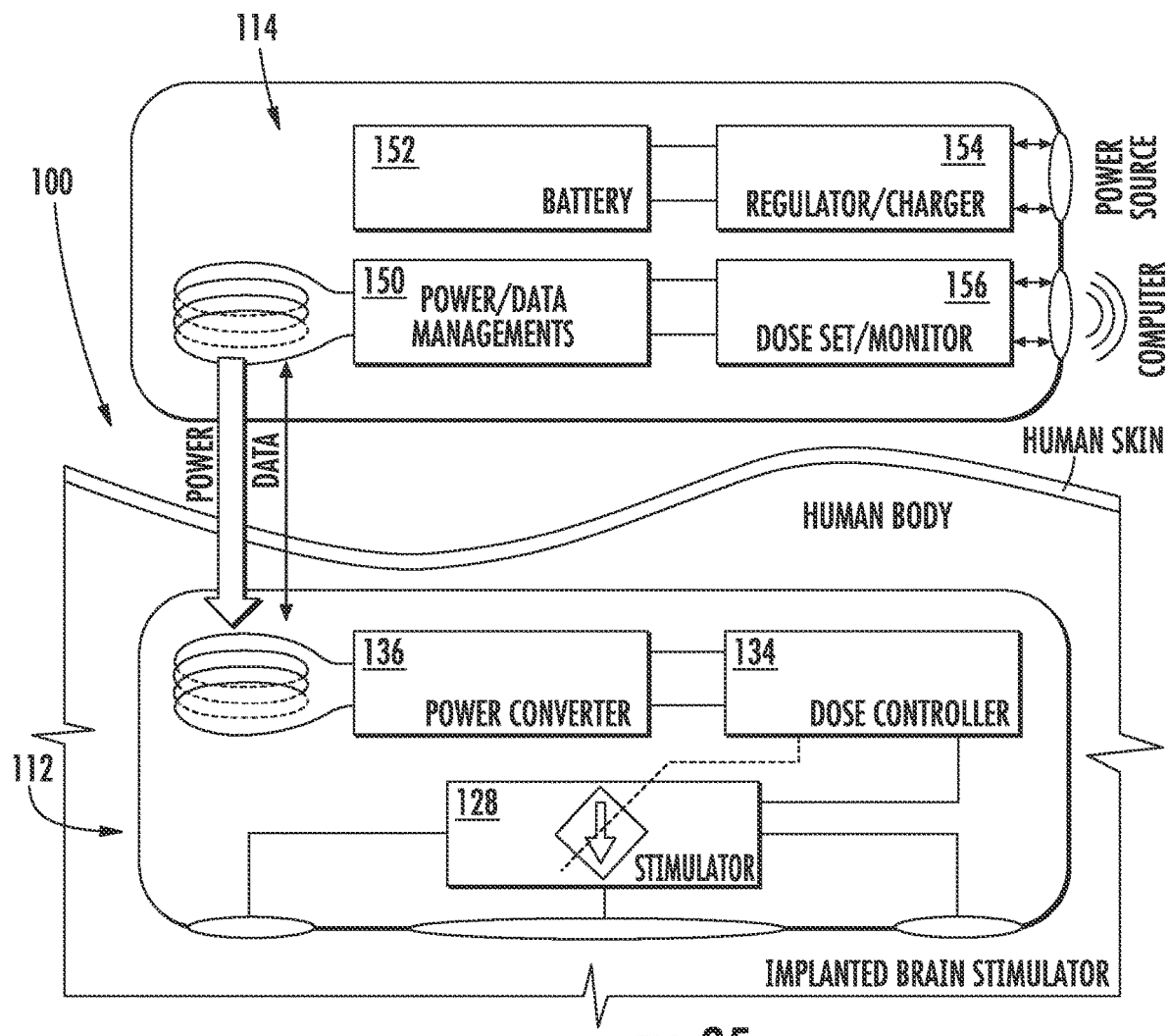
FIG. 25 illustrates a graphical view of the complete system containing implantable electrode with integrated stimulator which is implanted on target cortex and main controller outside of the body which provide power for implanted stimulator.

FIG. 25 illustrates a schematic diagram of the complete system containing implantable electrode with integrated stimulator which is implanted on target cortex and main controller outside of the body which provide power for implanted stimulator, according to an embodiment of the present invention. An implantable tDCS system composed of a power transmitter 150 and main controller 114 outside of the human body and a power receiver 136 inside of the body or patched on the human skin. FIG. 25 shows the proposed implantable device with a power transceiver 136, main controller 134, and stimulator 128. Power and data are transmitted between power converter transceiver 136 and power/data management module 150. The implanted brain stimulator 112 also includes a dose controller 134 and a stimulator 128. The external main controller 114 also includes a battery power source 152. The battery 152 is preferably rechargeable so the external main controller 114 also includes a power regulator/charger 154. The external main controller 14 includes a dose set monitor 156 for controlling the amount of stimulation applied. This can be set by the patient, a physician, nurse, caregiver etc. either on an external computing device or on the user interface of the external main controller 114, described herein.

It should be noted that the implantable device and the external main component can include a computing device such as a microprocessor, hard drive, solid state drive or any other suitable computing device known to or conceivable by one of skill in the art. The computing device can be programmed with a non-transitory computer readable medium that is programmed with steps to execute the different stimulation levels, patterns, and configurations available.

Any such computer application will be fixed on a non-transitory computer readable medium. It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for treatment of Parkinson's disease in a subject comprising:
   a first controller containing instructions regarding a predetermined force value that the subject is asked to create;
   a force transducer device having a plurality of transducers and configured to accept and measure forces, wherein one of the transducers is for a left hand of the subject and another of the transducers is for the right hand of the subject, wherein the force transducer device is configured to transmit data related to the accepted force to the first controller, and wherein the force transducer device is configured to receive instructions from the first controller regarding the predetermined force value that the subject is asked to create;
   a second controller that uses the measured forces to compute a laterality index; and
   a transcranial direct current stimulator configured to apply transcranial direct stimulation to motor cortices of the subject according to the laterality index, wherein for the subject with a negative laterality index, anodal stimulation is applied to the right motor cortex, and cathodal stimulation is applied to the left motor cortex, and for the subject with a positive laterality index, anodal stimulation is applied over the left motor cortex, and cathodal stimulation is applied to the right motor cortex.

2. The system of claim 1 further comprising a display screen for the force transducer device such that the subject can visualize the predetermined force value to be applied to the transducers.

3. The system of claim 1 wherein the transcranial direct current stimulation component comprises a headband for positioning the anode and the cathode and holding the transcranial direct current stimulation component on a head of the subject.

4. The system of claim 1 wherein communication between the transcranial direct current stimulation component and the first controller is wireless.

5. The system of claim 1 wherein the first controller comprises a computing device.

6. The system of claim 5 wherein the computing device comprises a non-transitory computer readable medium.

7. The system of claim 6 wherein the non-transitory computer readable medium is programmed to process data from the force transducer device and the transcranial direct stimulator.

* * * * *